US010092579B2

(12) United States Patent
Altaf et al.

(10) Patent No.: US 10,092,579 B2
(45) Date of Patent: Oct. 9, 2018

(54) GOLD(I) COMPLEXES WITH ANTICANCER PROPERTIES AND METHODS OF USE THEREOF

(71) Applicant: KING FAHD UNIVERSITY OF PETROLEUM AND MINERALS, Dhahran (SA)

(72) Inventors: Muhammad Altaf, Dhahran (SA); Muhammad Monim-Ul-Mehboob, Dhahran (SA); Anvarhusein Abdulkadir Isab, Dhahran (SA); Saleh Altuwaijri, AlKhobar (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 0 days.

(21) Appl. No.: 15/586,333

(22) Filed: May 4, 2017

(65) Prior Publication Data

US 2017/0232012 A1    Aug. 17, 2017

Related U.S. Application Data

(62) Division of application No. 14/990,509, filed on Jan. 7, 2016.

(51) Int. Cl.
| | |
|---|---|
| *A61K 31/66* | (2006.01) |
| *A61K 31/404* | (2006.01) |
| *A61K 31/506* | (2006.01) |
| *A61K 31/517* | (2006.01) |
| *A61K 31/44* | (2006.01) |
| *A61K 33/24* | (2006.01) |
| *A61K 39/395* | (2006.01) |
| *C07F 1/12* | (2006.01) |
| *C07F 9/50* | (2006.01) |

(52) U.S. Cl.
CPC ............ *A61K 31/66* (2013.01); *A61K 31/404* (2013.01); *A61K 31/44* (2013.01); *A61K 31/506* (2013.01); *A61K 31/517* (2013.01); *A61K 33/24* (2013.01); *A61K 39/395* (2013.01); *A61K 39/39558* (2013.01); *C07F 1/12* (2013.01); *C07F 9/5045* (2013.01)

(58) Field of Classification Search
CPC ...... A61K 31/66; A61K 33/24; A61K 31/404; A61K 31/44; A61K 31/506; A61K 31/517; A61K 39/395; A61K 39/39; A61K 39/39558; C07F 1/12; C07F 9/5045
See application file for complete search history.

(56) References Cited

U.S. PATENT DOCUMENTS

| | | | |
|---|---|---|---|
| 6,989,158 B1 | 1/2006 | Katti | |
| 8,895,611 B1 * | 11/2014 | Isab | ........................ A61K 31/28 514/495 |
| 2002/0119463 A1 * | 8/2002 | Faris | ..................... C12Q 1/6886 435/6.14 |
| 2008/0051414 A1 | 2/2008 | Hurley | |
| 2014/0142065 A1 * | 5/2014 | Che | ........................ C07F 9/5045 514/94 |

FOREIGN PATENT DOCUMENTS

CN        101781283 A  *  7/2010

OTHER PUBLICATIONS

Bao et. al., "Establishment of Human Gastric Cancer Cell Line (SGC-7901) Intraperitoneally Transplantable in Nude Mice", Recent Advances in Management of Digestive Cancers, 1993, Springer-Verlag Tokyo, pp. 416-418.*
Altaf, M., et al., "The Synthesis, Spectroscopic Characterization and Anticancer Activity of New Mono and Binuclear Phosphanegold(I) Oithiocarbamate Complexes", URL: http://pubs.rsc.org/en/Content/ArticleLanding/2015/NJ/c4nj00747#!divAbstract, New Journal of Chemistry, vol. 39, 5 Pages total. (2015) (Abstract only).
Valentina Gandin, et al., "Cancer cell death induced by phosphine gold(I) compounds targeting thioredoxin reductase", Biochemical Pharmacology, vol. 79, 2010, pp. 90-101.
Altaf et al., New Journal of Chemistry, publ. online Oct. 24, 2014, Royal Society of Chemistry, vol. 39(1), pp. 377-385.
Remington: The Science and Practice of Pharmacy, 2005, 21$^{st}$ ed., pp. 875-876, 1158.

* cited by examiner

*Primary Examiner* — Sarah Pihonak
(74) *Attorney, Agent, or Firm* — Oblon, McClelland, Maier & Neustadt, L.L.P.

(57) ABSTRACT

Monomeric and dimeric gold(I) complexes as anticancer agents. The gold(I) complexes are coordinated to mixed ligands: one phosphine-based ligand that may be monodentate or bidentate and at least one dithiocarbamate-based ligand that is monodentate. Pharmaceutical compositions incorporating the gold(I) complexes, methods of synthesis, methods of treating cancer and methods of inhibiting cancer cell proliferation and inducing cancer cell apoptosis are also provided.

5 Claims, 7 Drawing Sheets

GOLD(I) COMPLEXES WITH ANTICANCER PROPERTIES AND METHODS OF USE THEREOF

CROSS-REFERENCE TO RELATED APPLICATION

This application is a divisional application of U.S. patent application Ser. No. 14/990,509, filed on Jan. 7, 2016.

BACKGROUND OF THE INVENTION

Technical Field

The present invention relates to gold(I) complexes with anticancer or antitumor properties. More specifically, these gold(I) complexes can be either mono- or binuclear and each gold atom is coordinated to mixed ligands having different functional groups.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

The use of cisplatin and its analogues such as oxaliplatin and carboplatin as metal-based anticancer drugs is well acknowledged in the field of chemotherapy [B. Rosenberg, L. Van Camp and T. Krigas, Nature, 205 (1965) 698; N. Cutillas, G. S. Yellol, C. de Haro, C. Vicente, V. Rodriguez and J. Ruiz, Coord. Chem. Rev., 257 (2013) 2784; . D. Bugarčić, J. Bogojeski, B. Petrović, S. Hochreuther and R. Van Eldik, Dalton. Trans., 41 (2012) 12329; C. Vetter, C. Wagner, J. Schmidt and D. Steinborn, Inorg. Chim. Acta, 359 (2006) 4326; A. Casini and L. Messori, Curr. Top. Med. Chem. 11 (2011) 2647; E. Márta Nagy, L. Ronconi, C. Nardon and D. Fregona, Mini-Reviews in Med. Chem., 12 (2012) 1216—each incorporated herein by reference in its entirety]. These drugs have been used for the treatment of cancer patients worldwide. However, it is also known that cisplatin and its analogues have serious side effects, such as oto-, neuro-, and nephrotoxicity, which decrease its effectiveness in cancer therapy [S. Ahmad, A. A. Isab and S. Ali, Tradition Met. Chem., 31 (2006) 1003; S. R. McWhinney, R. M. Goldberg and H. L. McLeod, Mol. Cancer Ther., 8 (2009) 10; W. Liu and R. Gust, Chem. Soc. Rev. 42 (2013) 755; X. Yao, K. Panichpisal, N. Kurtzman, and K. Nugent, Am. J. Mod. Sci., 334 (2007) 115—each incorporated herein by reference in its entirety]. Consequently, gold(I) and gold(III) complexes had been investigated as non-platinum based anticancer candidates [S. S. Al-Jaroudi, M. Monim-ul-Mehboob, M. Altaf, M. Fettouhi, M. I. M. Wazeer, S. Altuwaijri and A. A. Isab, New J. Chem., (2014), DOI:10:1039/c3nj01624b; S. M. Janković, A. Djeković, . D. Bugarčić, S. V. Janković, G. Lukić, M. Folic and D. Čanović, Biometals, 25 (2012) 919; S. S. Al-Jaroudi, M. I. M. Wazeer, A. A. Isab and S. Altuwaijri, Polyhedron, 50 (2013) 434; R. B. Bostancioglu, K. Isik, H. Gene, K. Benkli and A. T. Koparal, J. Med. Chem., 27 (2012) 458—each incorporated herein by reference in its entirety].

The study of gold complexes, bearing different functional ligands exhibiting physical, chemical, biological and pharmacological properties, has gained much attention [S. S. Al-Jaroudi, M. Monim-ul-Mehboob, M. Altaf, M. Fettouhi, M. I. M. Wazeer, S. Altuwaijri and A. A. Isab, New J. Chem., (2014), DOI:10:1039/c3nj01624b; S. M. Janković, A. Djeković, . D. Bugarčić, S. V. Janković, G. Lukić, M. Folic and D. Čanović, Biometals, 25 (2012) 919; S. S. Al-Jaroudi, M. I. M. Wazeer, A. A. Isab and S. Altuwaijri, Polyhedron, 50 (2013) 434; R. B. Bostancioglu, K. Isik, VI. Gene, K. Benkli and A. T. Koparal, J. Med. Chem., 27 (2012) 458—each incorporated herein by reference in its entirety]. The gold(I) complexes have been studied as anti-arthritic and anti-microbial agents [O. Crespo, V. V. Brusko, M. C. Giameno, M. L. Tornil, A. Laguna and N. G. Zabirov, Eur. J. Inorg. Chem., (2004) 423; K. Nomiya, R. Noghochi and M. Oda, Inorg. Chim. Acta. 298 (2000) 24; H.-Q. Liu, T.-C. Cheung, S.-M. Peng and C.-M. Che, J. Chem. Soc., Chem. Comm., (1995) 1787; C. J. O'Connor and E. Sinn, Inorg. Chem., 17 (1978) 2067; M. A. Cinellu, G. Minghetti, M. V. Pinna, S. Stoccoro, A. Zucca, and M. Manassero, J. Chem. Soc., Dalton Trans., (1998) 1735—each incorporated herein by reference in its entirety]. For instance, the drugs like Auranofin, Solganol and Myocrisin have frequently been used for the treatment of rheumatoid arthritis [S. H. van Rijt and P. J. Sadler, Drug Discovery Today, 14 (2009) 1089; R. Noghuchi, A. Hara, A. Sugie and K. Nomiya, Inorg. Chem. Comm., 9 (2006) 355; K. Nomiya, R. Noghuchi, K. Ohsawa, K. Tsuda and M. Oda, J. Inorg. Biochem., 78 (2000) 363; B. P. Howe, Met.-Based Drugs., 4 (1997) 273; J. Ctalano and A. O. Etogo, J. Organomet. Chem., 690 (2005) 6041—each incorporated herein by reference in its entirety]. Interesting, the extensive cell-based (in vitro) and animal (in vivo) studies have revealed the potent anti-cancer activities of diverse classes of gold(I) and gold(III) complexes with a wide range of ligands against a panel of human cancer cell lines [J. C. Lima and L. Rodriguez, J. Med. Chem., 11 (2011) 921; C-M Che and R. W-Y. Sun, Chem. Commun., 47 (2011) 9554; P. Calami, A. Carotti, T. Guerri, L. Messori, E. Mini, P. Orioli and G. P. Speroni, J. Inorg. Biochem., 66 (1997) 103—each incorporated herein by reference in its entirety].

Bridged di-gold(I) complexes existing in a linear 2-coordinate configuration like [ClAu(P—P)AuCl] where P—P is a bisphosphine), tend to be more effective than free ligands and such complexes also lend to exhibit a broad range of anticancer activity [R. K. Johnson, C. K. Mirabelli, L. F. Faucette, F. L. McCabe, B. M. Sutton, D. L. Bryan, G. R. Girard and D. T. Hill, Proc. Amer. Assoc. Cancer Res., 26 (1985) 254; C. K. Mirabelli, L. F. Faucette, F. L. McCabe, B. M. Sutton, D. L. Bryan, G. R. Girard, D. T. Hill, J. O. Bartus, S. T. Crooke and R. K. Johnson, J. Med. Chem., 30 (1987) 2181—each incorporated herein by reference in its entirety]. This has inspired the synthesis of stable 4-coordinate digold(I) diphosphine complexes [S. J. Berners-Price, M. A. Mazid and P. J. Sadler, J. Chem. Soc., Dalton Trans., (1984) 969; S. J. Berners-Price and P. J. Sadler, Inorg. Chem., 25 (1986) 3822; D. T. Hill, G. R. Girard, U.S. Pat. No. 4,755,611, July 1988—each incorporated herein by reference in its entirety]. The effect of structural variation in chelated bis(diphosphate) gold(I) complexes [Au(R$_2$P(CH$_2$)$_n$PR$_2$)]X on their cytotoxicity and activity against P388 leukaemia, B16 melanoma and M5076 reticulum cell sarcoma has been studied [G. F. Rush, D. W. Albers, P. Meunies, K. Leffler, P. F. Smith, Toxicologist, 7 (1987) 59—incorporated herein by reference in its entirety]. J. W. Faamaua et al. reported compounds of general formula [(Ph$_2$P(CH$_2$)nPPh$_2$)(AuS$_2$CNR$_2$)$_2$], n=1, 2 or 3 and R=Et or c-hexyl [J. W. Faamaua and E. R. T. Tiekinka, J. Coord. Chem., 31(2) (1994) 93—incorporated herein by reference in its entirety].

Since the first decade of $21^{st}$ century, a new class of gold complexes with dithiocarbamate ligands has emerged as anticancer agents. In this regard, Fregona and coworkers synthesized and characterized some novel gold(III) compounds containing N,N-dimethyldithiocarbamate and ethyl sarcosine dithiocarbamate exhibiting potential chemical and biological profile [L. Ronconi, L. Giovagnini, C. Marzano, F. Bettio, R. Graziani, G. Pilloni, and D. Fregona, Inorg. Chem., 44 (2005) 1867—incorporated herein by reference in its entirety]. Dibromo(N,N-dimethyldithiocarbamato)gold (III) also showed a noteworthy inhibition of in-vivo MDA-MB-231 breast cancer growth [V. Milacic, D. Chen, L. Ronconi, K. R. Landis-Piwowar, D. Fregona and Q. P. Dou, Cancer Res., 66 (2006) 10478—incorporated herein by reference in its entirety]. Zhang et al. reported that gold(I)-dithiocarbamato species, namely [Au(ESDT)](2) could hamper the chymotrypsin-like activity of purified 20S proteasome and 26S proteasome in human breast cancer MDA-MB-231 cells, resulting in accumulation of ubiquitinated proteins and proteasome target proteins, and induction of cell death [X. Zhang, M. Frezza, V. Milacic, L. Ronconi, Y. Fan, C. Bi, D. Fregona and Q. P. Dou, J. Cell Biochem., 109 (2010) 162—incorporated herein by reference in its entirety]. Recently, the modern research has progressively targeted in search of new gold(I) complexes as potential anticancer drugs [S. Ahmad, A. A. Isab, S. Ali and A. R. Al-Arfaj, Polyhedron, 25 (2006) 1633; D. V. Partyka, T. J. Robilotto, M. Zeller, A. D. Hunter, T. G. Gray, Proc. Natl. Acad. Sci., (USA) 105 (2008) 14293; V. Wang, Q.-Y. He and C.-M. Che, J.-F. Chiu, Proteomics, 6 (2006) 131; Y. Shi, W. Chu, V. Wang, S. Wang, J. Du, J. Zhang, S. Li, G. Zhou, X. Qin and C. Zhang, Inorg. Chem. Comm., 30 (2013) 178; M. Monim-ul-Mehboob, M. Altaf, M. Fettouhi, A. A. Isab, M. I. M. Wazeer, M. N. Shaikh and S. Altuwaijri, Polyhedron, 61 (2003) 225—each incorporated herein by reference in its entirety].

Lung and colorectal cancers are frequent causes of cancer-related death in both males and females while cervix cancer is responsible for cancer deaths in females exclusively. Hence, there remains an unmet, dire need of new drugs to treat such lethal diseases through chemotherapy.

BRIEF SUMMARY OF THE INVENTION

According to a first aspect, the present disclosure provides a gold(I) complex having either of the following Formula 1 or Formula 2:

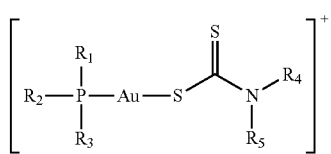

(Formula 1)

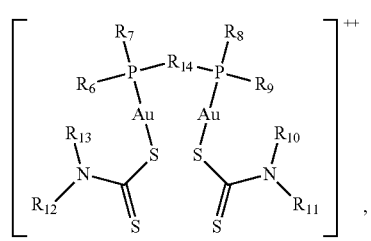

(Formula 2)

or a pharmaceutically acceptable salt, ester or prodrug thereof, $R_1$, $R_2$, $R_3$, $R_4$, $R_5$, $R_6$, $R_7$, $R_8$, $R_9$, $R_{10}$, $R_{11}$, $R_{12}$ and $R_{13}$ are each independently a linear or branched, substituted or unsubstituted $C_1$-$C_8$ alkyl group or a substituted or unsubstituted $C_6$-$C_8$ aryl group. $R_{14}$ is a methyl group or an ethyl group.

In one embodiment, $R_1$, $R_2$ and $R_3$ are each selected from the group consisting of a methyl group, an ethyl group, a propyl group, an n-butyl group, an isobutyl group, a sec-butyl group, a tert-butyl group, an n-pentyl group, an isopropyl group, a neopentyl group, a sec-pentyl group; a tert-pentyl group, an n-hexane group, an isohexane group and a neohexane group. $R_4$ and $R_5$ are each selected from the group consisting of a methyl group, an ethyl group, a phenyl group and a benzyl group. $R_6$, $R_7$, $R_8$, and $R_9$ are each selected from the group consisting of a phenyl group and a benzyl group. $R_{10}$, $R_{11}$, $R_{12}$ and $R_{13}$ are each selected from the group consisting of a methyl group, an ethyl group, a phenyl group and a benzyl group. $R_{14}$ is a methyl group or art ethyl group.

In one embodiment, the gold(I) complex has a formula selected from the group consisting of Formula 3, Formula 4, Formula 5 or Formula 6:

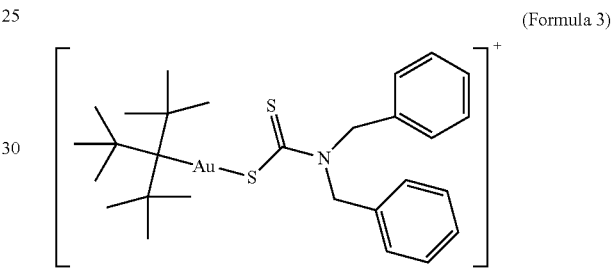

(Formula 3)

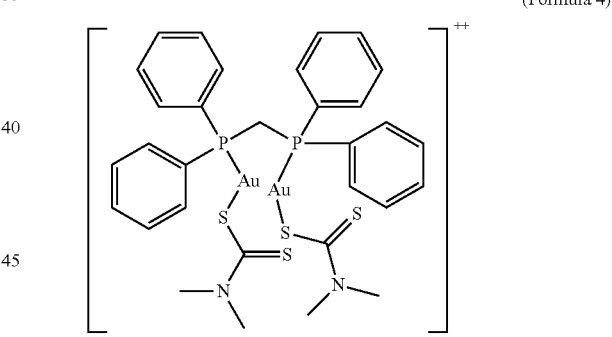

(Formula 4)

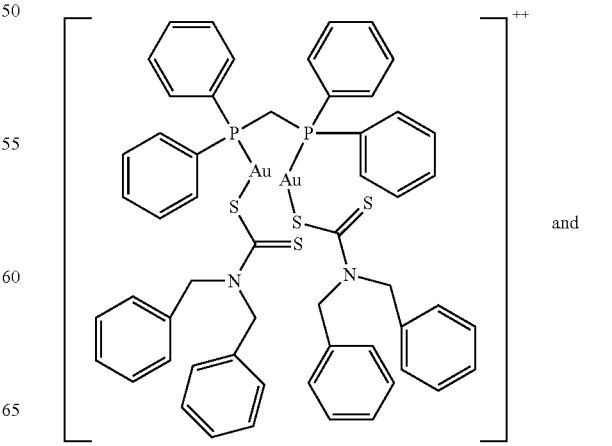

(Formula 5)

and (Formula 6)

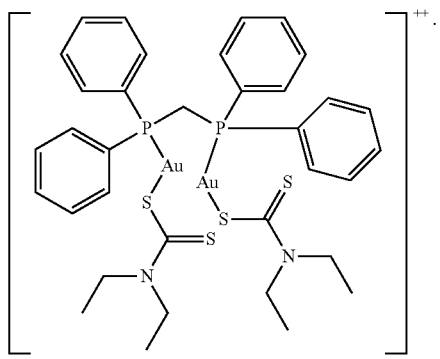

According to a second aspect, the present disclosure provides a composition comprising the gold(I) complex in accordance with the first aspect of the disclosure or a pharmaceutically acceptable salt, ester or prodrug thereof, and one or more pharmaceutically acceptable carriers.

In one embodiment, the pharmaceutical composition further comprises one or more other active pharmaceutical agents.

In one embodiment, the pharmaceutical composition is in solid, semi-solid or liquid dosage forms.

In one embodiment, the pharmaceutical composition is formulated for one or more modes of administration selected from the group consisting of oral administration, systemic administration, parenteral administration, inhalation spray, infusion, rectal administration, topical administration, intravesical administration, itradermal administration, transdermal administration, subcutaneous administration, intramuscular administration, intralesional administration, intracranial administration, intrapulmonal administration, intracardial administration, intrasternal administration and sublingual administration.

According to a third aspect, the present disclosure relates a method for inhibiting proliferation of cancer cells. The method comprises contacting the cancer cells with the gold(I) complex according to the first aspect of the disclosure or a pharmaceutically acceptable salt, ester or prodrug thereof.

In one or more embodiments, the cancer cells contacted with the gold(I) complex are human cells.

In one embodiment, the cancer cells are at least one selected from the group consisting of lung cancer cells, colorectal cancer cells and cervical cancer cells.

In one embodiment, the gold(I) complex concentration is 5-50 µM.

In one embodiment, the gold(I) complex exhibits an $IC_{50}$ of 1-150 µM for inhibiting the proliferation and inducing the apoptosis of the cancer cells.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1A:
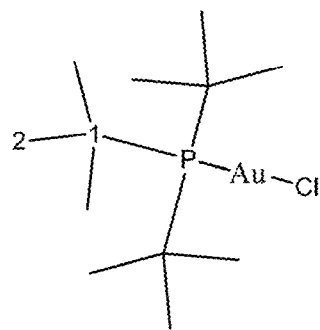
FIG. 1A illustrates the structure of mononuclear gold(I) precursor compound for Complex (A1), [t-$Bu_3$PAuCl].
Figure 1B:
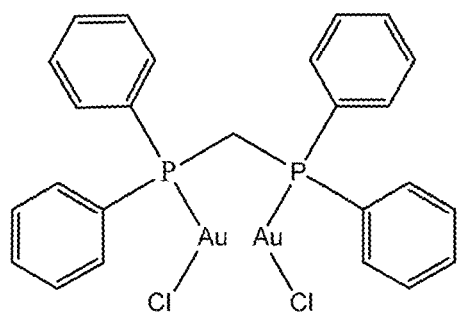
FIG. 1B illustrates the structure of binuclear gold(I) precursor compound for Complexes (A2)-(A4), [(DPPM)(AuCl)$_2$].
Figure 1C:
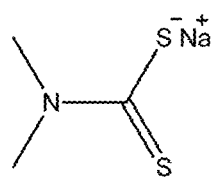
FIG. 1C illustrates the structure of dithiocarbamate ligand for Complex (A2) $NaS_2CN(CH_3)_2$.
Figure 1D:
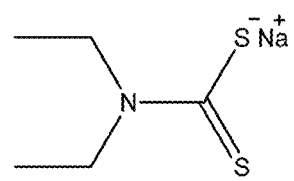
FIG. 1D illustrates the structure of dithiocarbamate ligand for Complex (A3), $NaS_2CN(C_2H_5)_2$.
Figure 1E:
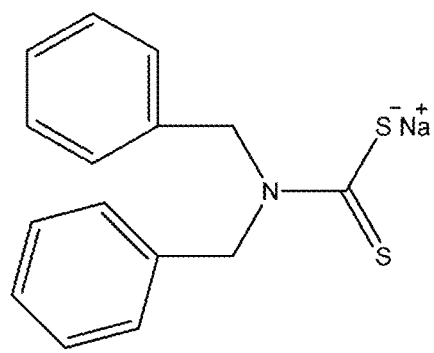
FIG. 1E illustrates the structure of dithiocarbamate ligand for Complexes (A1) and (A4), $NaS_2CN(C_7H_7)_2$.
Figure 2A:
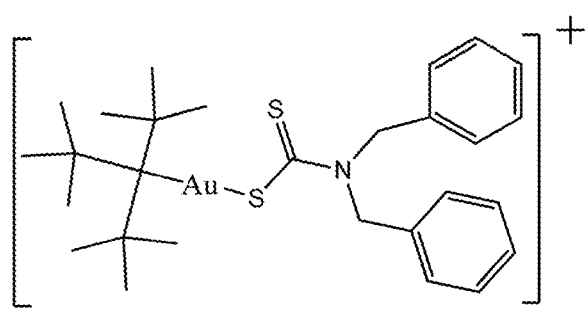
FIG. 2A shows the chemical structure of Complex (A1), [t-$Bu_3$PAu$S_2$CN($C_7H_7$)$_2$].
Figure 2B:
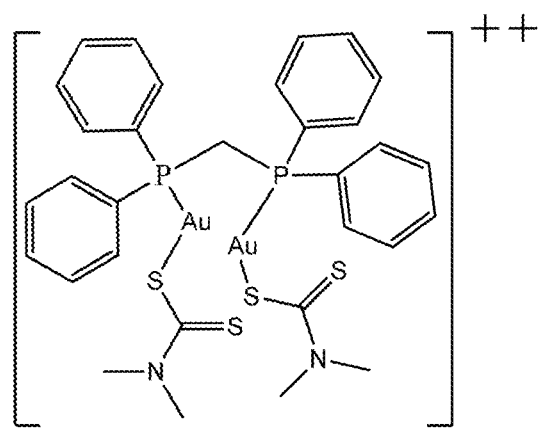
FIG. 2B shows the chemical structure of Complex (A2), [(DPPM)Au$_2$($S_2$CN($CH_3$)$_2$)$_2$].
Figure 2C:
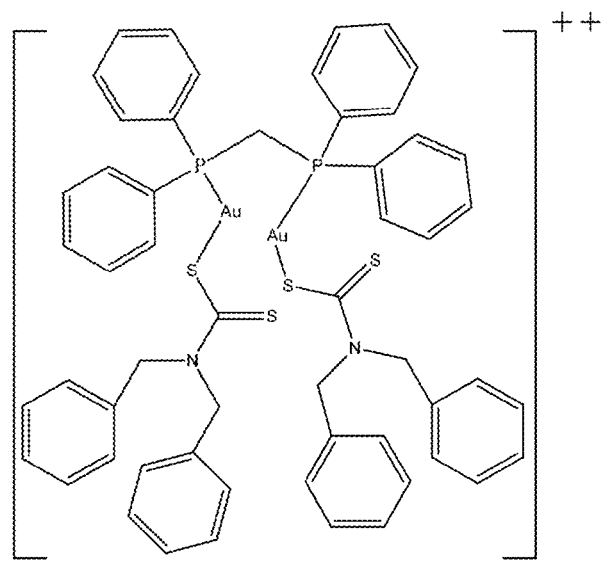
FIG. 2C shows the chemical structure of Complex (A3), [(DPPM)Au$_2$($S_2$CN($C_2H_5$)$_2$)$_2$].
Figure 2D:
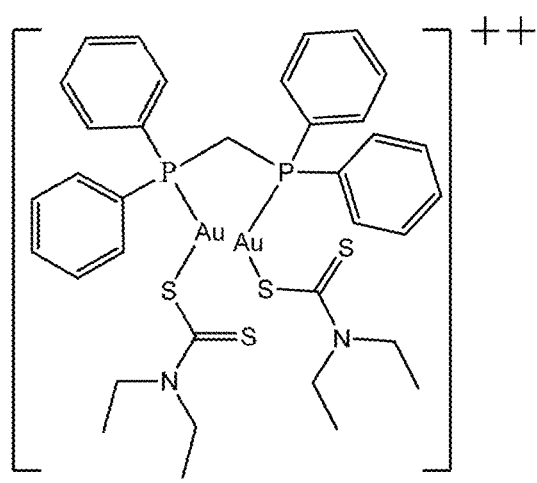
FIG. 2D shows the chemical structure of Complex (A4), [(DPPM)Au$_2$($S_2$CN($C_7H_7$)$_2$)$_2$].

Embodiments of the present disclosure will now be described more fully hereinafter with reference to the accompanying drawings, in which some, but not all embodiments of the disclosure are shown. Indeed, these disclosures may be embodied in many different forms and should not be construed as limited to the embodiments set forth herein; rather, these embodiments are provided so that the present disclosure will satisfy applicable legal requirements.

The present disclosure will be better understood with reference to the following definitions:

Definitions

As used herein, "compound" and "complex" are intended to refer to a chemical entity, whether in the solid, liquid or gaseous phase, and whether in a crude mixture or purified and isolated.

The term "alkyl", as used herein, unless otherwise specified, refers to a saturated straight, branched, or cyclic, primary, secondary, or tertiary hydrocarbon of typically $C_1$ to $C_8$, and specifically includes methyl, trifluoromethyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. The term optionally includes substituted alkyl groups. Moieties with which the alkyl group can be substituted are selected from the group consisting of hydroxyl, amino, alkylamino, arylamino, alkoxy, aryloxy, nitro, cyano, sufonic acid, sulfate, phosphonic acid, phosphate, or phosphoanate, either unprotected, or protected as necessary, as known to those skilled in the art, for example, as taught in Greene, et al., "Protective Groups in Organic Synthesis", John Wiley and Sons, Second Edition, 1991, hereby incorporated by reference in its entirety.

The term "aryl", as used herein, and unless otherwise specified, refers to phenyl, biphenyl, or naphthyl, and preferably phenyl. The term includes both substituted and unsubstituted moieties. The aryl group can be substituted with one or more moieties selected from the group consisting of hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., "Protective Groups in Organic Synthesis", John Wiley and Sons, Second Edition, 1991 hereby incorporated by reference in its entirety.

As used herein, "analogue" refers to a chemical compound that is structurally similar to a parent compound, but differs slightly in composition (e.g., one atom or functional group is different, added, or removed). The analogue may or may not have different chemical or physical properties than the original compound and may or may not have improved biological and/or chemical activity. For example, the analogue may be more hydrophilic or it may have altered reactivity as compared to the parent compound. The analogue may mimic the chemical and/or biologically activity of the parent compound (i.e., it may have similar or identical activity), or, in some cases, may have increased or decreased activity. The analogue may be a naturally or non-naturally occurring variant of the original compound. Other types of analogues include isomers (enantiomers, diastereomers, and the like) and other types of chiral variants of a compound, as well as structural isomers.

As used herein, "derivative" refers to a chemically or biologically modified version of a chemical compound that is structurally similar to a parent compound and (actually or theoretically) derivable from that parent compound. A "derivative" differs from an "analogue" in that a parent compound may be the starting material to generate a "derivative," whereas the parent compound may not necessarily be used as the starting material to generate an "analogue." A derivative may or may not have different chemical or physical properties of the parent compound. For example, the derivative may be more hydrophilic or it may have altered reactivity as compared to the parent compound. Derivatization (i.e., modification) may involve substitution of one or more moieties within the molecule (e.g., a change in functional group). The term "derivative" also includes conjugates, and prodrugs of a parent compound (i.e., chemically modified derivatives which can be converted into the original compound under physiological conditions).

The term "prodrug" refers to an agent that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis [Harper, N. J. (1962). Drug Latentiation in Jucker, ed. Progress in Drug Research, 4:221-294; Morozowich et al. (1977). Application of Physical Organic Principles to Prodrug Design in E. B. Roche ed. Design of Biopharmaceutical Properties through Prodrugs and Analogs, APhA; Acad. Pharm. Sci.; E. B. Roche, ed. (1977). Bioreversible Carriers in Drug in Drug Design, Theory and Application, APhA; H. Bundgaard, ed. (1985) Design of Prodrugs, Elsevier; Wang et al. (1999) Prodrug approaches to the improved delivery of peptide drug, *Curr. Pharm. Design.* 5(4):265-287; Pauletti et al. (1997). Improvement in peptide bioavailability: Peptidomimetics and Prodrug Strategies, *Adv. Drug. Delivery Rev.* 27:235-256; Mizen et al. (1998). The Use of Esters as Prodrugs for oral Delivery of β-Lactam antibiotics, *Pharm. Biotech.* 11:345-365; Gaignault et al. (1996). Designing Prodrugs and Bioprecursors I. Carrier Prodrugs, *Pract. Med. Chem.* 671-696; M. Asgharnejad (2000). Improving Oral Drug Transport Via Prodrugs, in G. L. Amidon, P. I. Lee and E. M. Topp, Eds., Transport Processes in Pharmaceutical Systems, Marcell Dekker, p. 185-218; Balant et al. (1990) Prodrugs for the improvement of drug absorption via different routes of administration, *Eur. J. Drug Metab. Pharmacokinet.,* 15(2): 143-53; Balimane and Sinko (1999). Involvement of multiple transporters in the oral absorption of nucleoside analogues, *Adv. Drug Delivery Rev.,* 39(1-3):183-209; Browne (1997). Fosphenyloin (Cerebyx), *Clin. Neuropharmacol.* 20(1): 1-12; Bundgaard (1979). Bioreversible derivatization of drugs—principle and applicability to improve the therapeutic effects of drugs, *Arch. Pharm. Chemi.* 86(1): 1-39; H. Bundgaard, ed. (1985) Design of Prodrugs, New York: Elsevier; Fleisher et al. (1996). Improved oral drug delivery: solubility limitations overcome by the use of prodrugs. *Adv. Drug Delivery Rev.* 19(2): 115-130; Fleisher et al. (1985). Design of prodrugs for improved gastrointestinal absorption by intestinal enzyme targeting, *Methods Enzymol.* 112: 360-81; Farquhar D, et al. (1983). Biologically Reversible Phosphate-Protective Groups, *J. Pharm. Sci.,* 72(3): 324-325; Han, H. K. et al. (2000). Targeted prodrug design to optimize drug delivery, *AAPS PharmSci.* 2(1): E6; Sadzuka Y. (2000). Effective prodrug liposome and conversion to active metabolite, *Curr. Drug Metab.,* 1(1):31-48; M. Lambert (2000) Rationale and application of lipids as prodrug carrier, *Eur. J. Pharm. Sci.,* 11 Suppl 2:S15-27; Wang, W. et al. (1999) Prodrug approaches to the improved delivery of peptide drugs. *Curr. Pharm. Des.,* 5(4):265-87—each incorporated herein by reference in its entirety]. In some embodiments, "Pharmaceutically acceptable prodrugs" refer to a compound that is metabolized, for example hydrolyzed or oxidized, in the host to form the pharmaceutical composition of the present disclosure. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehyrolyzed, alkylated, dealkylated, acylated, deacylated, phosphorylated, dephosphorylated to produce the active compound.

The term "therapeutically effective amount" as used herein refers to that amount of the compound being administered which will relieve to some extent one or more of the symptoms of the disorder being treated. In reference to cancer or pathologies related to increased cell division, a therapeutically effective amount refers to that amount which has the effect of at least one of the following: (1) reducing the size of a tumor, (2) inhibiting (that is, slowing to some extent, preferably stopping) aberrant cell division, growth or proliferation, for example cancer cell division, (3) preventing or reducing the metastasis of cancer cells, (4) relieving to some extent (or, preferably, eliminating) one or more symptoms associated with a pathology related to or caused in part by unregulated or aberrant cellular division, including for example, cancer and (5) inducing apoptosis of cancer cells or tumor cells.

As used herein, the terms "therapies" and "therapy" can refer to any method(s), composition(s), and/or agent(s) that can be used in the prevention, treatment and/or management of a cancer or one or more symptoms thereof.

As used herein, the terms "treat," "treatment," and "treating" in the context of the administration of a therapy to a subject in need thereof refer to the reduction or inhibition of the progression and or duration of cancer, the reduction or amelioration of the severity of cancer, and/or the amelioration of one or more symptoms thereof resulting from the administration of one or more therapies. In some embodiments, the subject is a mammalian subject. In one embodiment, the subject is a human. "Treating" or "treatment" of a disease includes preventing the disease from occurring in a subject that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease). With regard to cancer or hyperplasia, these terms simply mean that the life expectancy of an individual affected with a cancer will be increased or that one or more of the symptoms of the disease will be reduced. In specific embodiments, such terms refer to one, two or three or more results following the administration of one, two, three or more therapies: (1) a stabilization, reduction or elimination of the cancer stem cell population; (2) a stabilization, reduction or elimination in the cancer cell population; (3) a stabilization or reduction in the growth of a tumor or neoplasm; (4) an impairment in the formation of a tumor; (5) eradication, removal, or control of primary, regional and/or metastatic cancer; (6) a reduction in mortality; (7) an increase in disease-free, relapse-free, progression-free, and/or overall survival, duration, or rate; (8) an increase in the response rate, the durability of response, or number of patients who respond or are in remission; (9) a decrease in hospitalization rate, (10) a decrease in hospitalization lengths, (11) the size of the tumor is maintained and does not increase or increases by less than 10%, preferably less than 5%, preferably less than 4%, preferably less than 2%, and (12) an increase in the number of patients in remission. In certain embodiments, such terms refer to a stabilization or reduction in the cancer stem cell population. In some embodiments, such terms refer to a stabilization or reduction in the growth of cancer cells. In some embodiments, such terms refer to stabilization or reduction in the cancer stem cell population and a reduction in the cancer cell population. In some embodiments, such terms refer to a stabilization or reduction in the growth and or formation of a tumor. In some embodiments, such terms refer to the eradication, removal, or control of primary, regional, or metastatic cancer (e.g., the minimization or delay of the spread of cancer). In some embodiments, such terms refer to a reduction in mortality and/or an increase in survival rate of a patient population. In further embodiments, such terms refer to an increase in the response rate, the durability of response, or number of patients who respond or are in remission. In some embodiments, such terms refer to a decrease in hospitalization rate of a patient population and/or a decrease in hospitalization length for a patient population.

"Pharmaceutically acceptable salt" or "pharmaceutically acceptable ester" refers to a compound in a pharmaceutically acceptable form such as an ester, a phosphate ester, a salt of an ester or a related) which, upon administration to a subject in need thereof, provides at least one of the gold(I) complexes deserved herein. Pharmaceutically acceptable salts and ester retain the biological effectiveness and properties of the free bases and which are obtained by reaction with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid, malic acid, maleic acid, succinic acid, tartaric acid, citric acid, and the like. Suitable salts include those derived from alkali metals such as potassium and sodium, alkaline earth metals such as calcium and magnesium, among numerous other acids well known in the art.

A "pharmaceutical composition" refers to a mixture of the compounds described herein or pharmaceutically acceptable salts, esters or prodrugs thereof, with other chemical components, such as physiologically acceptable carriers and excipients. One purpose of a pharmaceutical composition is to facilitate administration of at least one gold(I) complex to a subject.

As used herein, a "pharmaceutically acceptable carrier" refers to a carrier or diluent that does not cause significant irritation to an organism and does not abrogate the biological activity and properties of the administered gold(I) complex. the term carrier encompasses any excipient, diluent, filler, salt, buffer, stabilizer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., Remington's Pharmaceutical Sciences, 21st Edition, ed. University of the Sciences in Philadelphia, Lippincott, Williams & Wilkins, Philadelphia Pa., 2005, which is incorporated herein by reference in its entirety. Examples of physiologically acceptable carriers include buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN® (ICI, Inc.; Bridgewater, N.J.), polyethylene glycol (PEG), and PLURONICS™ (BASF; Florham Park, N.J.).

An "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

The terms "including", "such as", "for example" and the like are intended to refer to exemplary embodiments and not to limit the scope of the present disclosure.

Gold(I) Complexes and Pharmaceutical Compositions Thereof

The present disclosure provides mono- and di-gold(I) complexes having medicinal or pharmaceutical properties, preferably antitumor or anticancer properties. In these monomeric or binuclear gold(I) complexes, each gold(I) atom is coordinated, preferably chelated by two or more mixed ligands that are based on phosphine or dithiocarbamate functional groups as shown below:

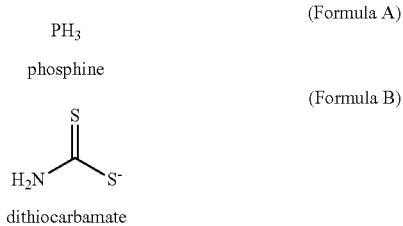

The phosphine-based ligand can be either monodentate (i.e. monophosphine and having one P donor atom) or bidentate (i.e. bisphosphine and having two P donor atoms) and include derivatives thereof. The bisphosphine ligand further includes a bridging short alkyl group between the phosphorus atoms, for example, a methyl or an ethyl group.

The dithiocarbamate-based ligand, on the other hand, coordinates or chelates a gold(I) atom in a monodentate manner. The nitrogen atom of a dithiocarbamate-based ligand can be substituted with one or more alkyl or aryl groups, for example, substituted or unsubstituted $C_1$-$C_8$ alkyl groups or substituted or unsubstituted $C_6$-$C_8$ aryl groups.

Hence, a phosphine gold(I) dithiocarbamate complex provided by the present disclosure has a generic formula of either Formula 1 or Formula 2:

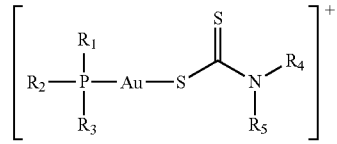

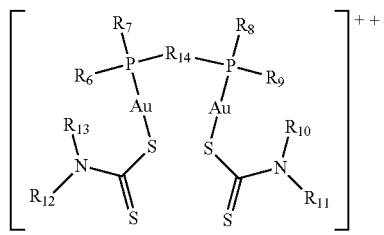

where;
the complex is either mononuclear or binuclear having one or two gold atoms;
each of the gold atoms is coordinated with one P donor atom from a phosphine-based ligand and one S donor atom from a dithiocarbamate-based ligand;
$R_1$, $R_2$, $R_3$, $R_4$, $R_5$, $R_6$, $R_7$, $R_8$, $R_9$, $R_{10}$, $R_{11}$, $R_{12}$ and $R_{13}$ are each independently a linear or branched, substituted or unsubstituted $C_1$-$C_8$ alkyl group or a substituted or unsubstituted $C_6$-$C_8$ aryl group; and
$R_{14}$ is a methyl group or an ethyl group.

A monomeric phosphine gold(I) dithiocarbamate complex contains one S—Au—P motif whereas a dimeric phosphine gold(I) dithiocarbamate complex contains two of the structural motifs. The Au—S and Au—P bond distances are equal or nearly equal to each other at 1.8-2.8 Å, preferably 1.8-2.5 Å, more preferably 1.8-2.3 Å, even more preferably 2-2.3 Å.

In some embodiments, a phosphine gold(I) dithiocarbamate complex in accordance with the present disclosure has a generic formula of either Formula 1 or Formula 2. The complex is either mononuclear or binuclear having one or two gold atoms. Each of the gold atoms is coordinated with one P donor atom from a phosphine-based ligand and one S donor atom from a dithiocarbamate-based ligand, where:

$R_1$, $R_2$ and $R_3$ are each selected from the group consisting of a methyl group, an ethyl group, a propyl group, an n-butyl group, an isobutyl group, a sec-butyl group, a tert-butyl group, an n-pentyl group, an isopropyl group, a neopentyl group, a sec-pentyl group; a tert-pentyl group, an n-hexane group, an isohexane group and a neohexane group;

$R_4$ and $R_5$ are each selected from the group consisting of a methyl group, an ethyl group, a phenyl group and a benzyl group;

$R_6$, $R_7$, $R_8$ and $R_9$ are each selected from the group consisting of a phenyl group and a benzyl group;

$R_{10}$, $R_{11}$, $R_{12}$ and $R_{13}$ are each selected from the group consisting of a methyl group, an ethyl group, a phenyl group and a benzyl group; and $R_{14}$ is a methyl group or an ethyl group.

In one embodiment, a phosphine gold(I) dithiocarbamate complex of the present disclosure is according to one of the following Formulas 3-6:

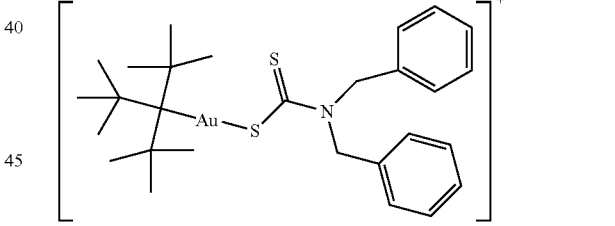

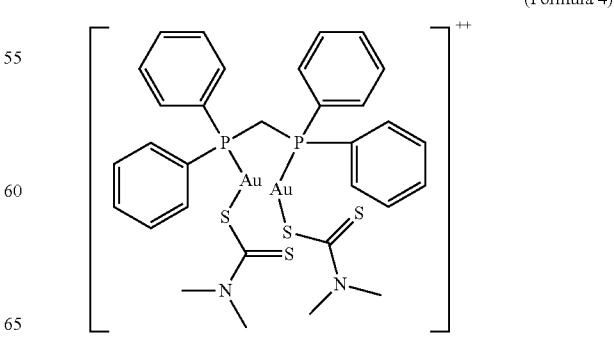

(Formula 5)

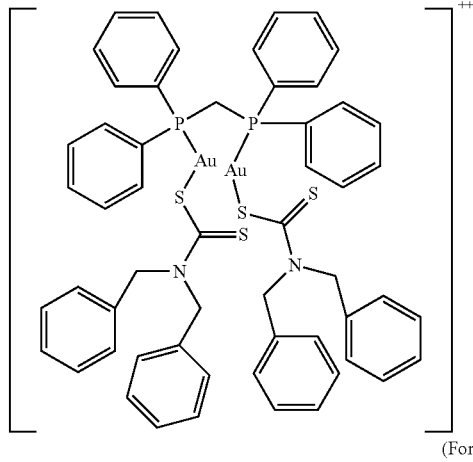

(Formula 6)

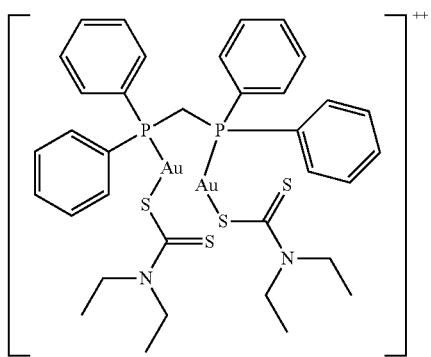

In this embodiment, the phosphine gold(I) dithiocarbamate complex is one of the following:

tri-tert-butyl-phosphine gold(I) dibenzyldithiocarbamate (Formula 5), 1,1-bis(diphenylphosphino)methane digold(I) dimethyldithiocarbamate (Formula 6), 1,1-bis(diphenylphosphino)methane digold(I) diethyldithiocarbamate (Formula 7), and 1,1-bis(diphenylphosphino)methane digold(I) dibenzyldithiocarbamate (Formula 8).

In certain embodiments, especially but not limited to pharmaceutical applications, the phosphine gold(I) dithiocarbamate complex can further include a counter-anion to form a pharmaceutically acceptable salt. As used herein, the term "counter-anion" refers to an anion, preferably a pharmaceutically acceptable anion that is associated with a positively charged mononuclear or binuclear phosphine gold (I) dithiocarbamate complex of at least one of the Formulas 3-8. Non-limiting examples of counter-anions include halides such as fluoride, chloride, bromide, iodide; nitrate; sulfate; phosphate; methanesulfonate; ethanesulfunate; p-toluenesulfonate, salicylate, malate, maleate, succinate, tartarate; citrate; acetate; perchlorate; trifluoromethanesulfonate (triflate); acetylacetonate; hexafluorophosphate; and hexafluoroacetylacetonate. In some embodiments, the counter-anion is a halide, preferably chloride.

Another aspect of the present disclosure relates to pharmaceutical composition comprising one or more of the phosphine gold(I) dithiocarbamate complexes described herein. In other words, the gold(I) complexes described herein or analogues or derivatives thereof can be provided in a pharmaceutical composition. Depending on the intended mode of administration, the pharmaceutical composition can be in the form of solid, semi-solid or liquid dosage forms, such as, for example, tablets, suppositories, pills, capsules, powders, liquids, or suspensions, preferably in unit dosage form suitable for single administration of a precise dosage. The compositions will include a therapeutically effective amount of one or more of the gold(I) complexes described herein or derivatives thereof in combination with a pharmaceutically acceptable carrier and, in addition, may include other medicinal agents, pharmaceutical agents, carriers, diluents or other non-active ingredients. By pharmaceutically acceptable is meant a material that is not biologically or otherwise undesirable, which can be administered to an individual along with the selected compound without causing significant unacceptable biological effects or interacting in a deleterious manner with the other components of the pharmaceutical composition in which it is contained.

A phosphine gold(I) dithiocarbamate complex or an analogue or derivative thereof may be used in conjunction with one or more additional compounds, in the treatment or prevention of neoplasm; of tumor or cancer cell division, growth, proliferation and/or metastasis in a mammalian subject; inhibition of thioredoxin reductase (TrxR) activity in tumor and/or cancer cells; induction of death or apoptosis of tumor and/or cancer cells; and/or any other form of proliferative disorder. A gold(I) complex of the present disclosure can be formulated as a pharmaceutical composition.

It has been reported that thiol/selenol containing proteins, like thioredoxin reductase (TrxR), are the major targets for gold(I) based anticancer agents. An accepted mechanism of action is that phosphine gold(I) complexes act as irreversible inhibitors of at least the mammalian mitochondrial thioredoxin reductase (TrxR2), whose expression is elevated in cancer cells, thereby leading to the eventual death of the cancer cells [J. C. Lima and L. Rodriguez, J. Med. Chem., 11 (2011) 921; S. Urig, K. Fritz-Wolf, R. Réau, C. Herold-Mende, K. Tóth, E. Davioud-Charvet and K. Becker, Angew. Chem. Int. Ed. 45 (2006) 1881; V. Gandin, A. P. Fernandes, M. P. Rigobello, B. Dani, F. Sorrentino, F. Tisato, M. Björnstedt, A. Bindoli, A. Sturaro, R. Relia and C. Marzano, Biochem Pharmacol 79 (2010) 90; Omata, Yo; Folan, Matt; Shaw, Melissa; Messer, Regina L.; Lockwood, Petra E.; Hobbs, David; Bouillaguet, Serge; Sano, Hidehiko; Lewis, Jill B.; Wataha, John C, Toxicology in vitro 20 (2006) 882—each incorporated herein by reference in its entirety]. Other Trx reductases that may also be inhabited by phosphine gold(I) complexes are cytosolic Trx reductase (TrxR1), testis specific TrxR3, glutathione-disulfide reductase (GSR) and trypanothione reductase.

The neoplastic activity of the tumor or cancer cells may be localized or initiated in one or more of the following: blood, brain, bladder, lung, cervix, ovary, colon, rectum, pancreas, skin, prostate gland, stomach, breast, liver, spleen, kidney, head, neck, testicle, bone (including bone marrow), thyroid gland, central nervous system. The phosphine gold (I) dithiocarbamate complex of the present disclosure or the pharmaceutical composition thereof is especially effective in the treatment or prevention of colorectal cancer (including colon cancer, rectum cancer and bowel cancer); lung cancer (including non-small cell lung carcinoma or NSCLC and small cell lung carcinoma); cervical cancer (including the histologic subtypes of squamous cell carcinoma, adenocarcinoma, adenosquamous carcinoma, small cell carcinoma, neuroendocrine tumor, glass cell carcinoma, villoglandular adenocarcinoma, melanoma and lymphoma).

A pharmaceutical composition comprising one or more gold(I) complexes of the present disclosure can then be administered orally, systemically, parenterally, by inhalation spray, rectally, or topically in dosage unit formulations containing conventional nontoxic pharmaceutically acceptable carriers, adjuvants, and vehicles as desired. In some embodiments, the method of administration of the steroid or an analogue or derivative thereof is oral. In other embodiments, the compound or an analogue or derivative thereof is administered by injection, such as, for example, through a peritumoral injection.

Topical administration can also involve the use of transdermal administration such as transdermal patches or iontophoresis devices. The term parenteral as used herein includes intravesical, intradermal, transdermal, subcutaneous, intramuscular, intralesional, intracranial, intrapulmonal, intracardial, intrasternal and sublingual injections, or infusion techniques. Formulation of drugs is discussed in, for example, Hoover, John E., Remington's Pharmaceutical Sciences, Mack Publishing Co., Easton, Pa.; 1975. Another example of includes Liberman, H. A. and Lachman, L., Eds., Pharmaceutical Dosage Forms, Marcel Decker, New York, N.Y., 1980, which is incorporated herein by reference in its entirety.

Injectable preparations, for example, sterile injectable aqueous or oleaginous suspensions can be formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables. Dimethyl acetamide, surfactants including ionic and non-ionic detergents, polyethylene glycols can be used. Mixtures of solvents and wetting agents such as those discussed above are also useful. Suppositories for rectal administration of the compound or an analogue or derivative thereof can be prepared by mixing the steroid or an analogue or derivative thereof with a suitable nonirritating excipient such as cocoa butter, synthetic mono- di- or triglycerides, fatty acids and polyethylene glycols that are solid at ordinary temperatures but liquid at the rectal temperature and will therefore melt in the rectum and release the drug.

Solid dosage forms for oral administration can include capsules, tablets, pills, powders, and granules. In such solid dosage forms, the compounds of this disclosure are ordinarily combined with one or more adjuvants appropriate to the indicated route of administration. If administered per os, a contemplated steroid or an analogue or derivative thereof can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering agents such as sodium citrate, magnesium or calcium carbonate or bicarbonate. Tablets and pills can additionally be prepared with enteric coatings.

For therapeutic purposes, formulations for parenteral administration can be in the form of aqueous or non-aqueous isotonic sterile injection solutions or suspensions. These solutions and suspensions can be prepared from sterile powders or granules having one or more of the carriers or diluents mentioned for use in the formulations for oral administration. A contemplated steroid or an analogue or derivative thereof of the present disclosure can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending, agents, and sweetening, flavoring, and perfuming agents.

The amount of active ingredient that can be combined with the carrier materials to produce a single dosage form varies depending upon the mammalian subject treated and the particular mode of administration.

Methods of Synthesis

The mono- and di-gold(I) complexes having mixed phosphine-based and dithiocarbamate-based ligands as described herein are not limited by their synthesis routes and methods. The gold(I) complexes with ligands having dithiocarbamate and phosphine functionalities can be prepared by previously reported synthesis and methods with slight modifications as recognized as appropriate by a person of ordinary skill in the pharmaceutical or medicinal chemistry art [U.S. Pat. Appl. Pub. US2014/0142065A1; F. K. Keter, I. A. Guzei, M. Nell; W. E. van Zyl and J. Darkwa, Inorg. Chem, 53 (2014) 2058; C. Li, "Gold(I) and Gold(III) Phosphine Complexes Exhibiting Weak $Au^1$ . . . $Au^1$ Interactions and Unsupported $Au^{11}$—$Au^{11}$ Bonds—Synthesis, Spectroscopy, Host-Guest Chemistry and Reactivity Studies", A thesis submitted in partial fulfillment of the requirements for the Degree of Doctor of Philosophy at The University of Hong Kong (2001) 1; P. Tadbuppa, "Phosphinegold(I) thiolates: Synthesis and Biological Activities", A thesis submitted for the degree of Doctor of Philosophy at the National University of Singapore (2009) 1—each incorporated herein by reference in its entirety].

In one embodiment, the gold(I) complexes of the present disclosure are prepared using monomeric or dimeric phosphinegold(I) precursor compounds and dialkyl- or diaryldithiocarbamate sodium or potassium anhydrous or hydrated sails. With the gold(I) precursor compounds, a monomeric gold(I) precursor compound beats a monophosphine monodentate ligand and a halide ligand while a dimeric gold(I) precursor compound carries a bisphosphine bisdentate ligand and two halide ligands. The gold(I) precursor compound and the dithiocarbamate salt are mixed in an organic solvent such as ethanol or acetone at room temperature and the reaction mixture is continuously stirred for 2-4 h. The obtained solution at the end of the stirring is pale/light yellow and is either clear or turbid. The turbidity can be removed by addition of a few drops up to 5 mL of water (preferably distilled and deionized). The solution is filtered and left to crystallize by slow evaporation at room temperature. Colorless or yellow crystal or semi-crystalline products are obtained after 3-7 days.

Method of Inhibiting Proliferation of Cancer Cells and Inducing Cancer Cell Death The present disclosure further provides a method of inhibiting proliferation of human cancer cells and inducing apoptosis of the human cancer cells in vitro or in vivo. Human cancer cells are contacted with 1-100 µM of gold(I) complex in accordance with the present disclosure or a composition comprising the gold(I) complex at the defined concentration range, preferably 2-75 µM, more preferably 5-50 µM, even more preferably 5-10 µM, 10-25 µM, 5-25 µM, 25-50 µM and 10-50 µM. The viability of cells can be determined by standard cell viability assays such as but not limited to ATP test, Calcein AM assay, clonogenic assay, ethidium homodimer assay, Evans blue assay, Fluorescein diacetate hydrolysis/propidium iodide staining assay, flow cytometry assay, formazan-based assays (MTT.XTT), green fluorescent protein assay, lactate dehydrogenase assay, methyl vilet assay, propidium iodide assay, Resazurin assay, Trypan Blue assay and TUNEL assay.

When contacted with the gold(I) complex at the defined concentration, the viability of the human cancer cells is reduced to at least 95%, preferably at least 85%, more preferably at least 75%, even more preferably at least 50%, at least 45%, at least 40%, at least 35%, at least 30%, at least 25%, at least 20%, most preferably at least 15%, at least 12.5%, at least 10%, at least 7.5%, at least 5%, at least 2.5%, at least 2%, at least 1% and at least 0.5%.

The half maximal inhibitory concentration ($IC_{50}$) values of the gold(I) complexes against the human cancer cells are no higher than 150 µM, preferably at least no higher than 100 µM, more preferably no higher than 50 µM, no higher than 30 µM, even more preferably no higher than 15 µM, no higher than 12 µM, most preferably no higher than 10 µM, no higher than 5 µM and no higher than 2 µM. In some embodiments, compared to cisplatin, the $IC_{50}$ values of the gold(I) complexes provided herein are at least 2 times lower, preferably 2 to 15 times lower, more preferably 3 to 15 times lower, even more preferably 5 to 15 times lower.

In some embodiments, the human cancer cells are derived from commercial cell line models, including but are not limited to HeLa cervical cancer cells, A549 lung cancer cells, HCT-15 colon cancer cells, HCT-8 or HRT-8 colon cancer cells, DLD-1 colon cancer cells, MCF-7 breast cancer cells, A2780 ovarian cancer cells, A2780-cis cisplatin-resistant ovarian cancer cells, PC-3 prostatic cancer cells, DU-145 prostatic cancer cells, SGC7907 gastrointestinal cancer cells.

In other embodiments, the human cancer cells are cancer cells of a human patient who has been diagnosed with, is suspected of having, or is susceptible to or at risk of having at least one form of cancer, preferably colorectal cancer, cervical cancer and/or lung cancer.

Methods of Treating Cancers and Combination Therapies

Cancers such as but not limited to sarcomas, carcinomas, melanomas, myelomas, gliomas and lymphomas can be treated or prevented with the gold(I) complexes provided herein. In some embodiments, methods incorporating the use of at least one of the gold(I) complexes of the present disclosure are effective in the treatment or prevention of cancer of the blood, brain, bladder, lung, cervix, ovary, colon, rectum, pancreas, skin, prostate gland, stomach, breast, liver, spleen, kidney, head, neck, testicle, bone (including bone marrow), thyroid gland or central nervous system. In some embodiments, these methods are especially effective in the treatment or prevention of cervical, colon and lung cancers.

The methods for treating cancer and other proliferative disorders described herein inhibit, remove, eradicate, reduce, regress, diminish, arrest or stabilize a cancerous tumor, including at least one of the tumor growth, tumor cell viability, tumor cell division and proliferation, tumor metabolism, blood flow to the tumor and metastasis of the tumor. In some embodiments, after treatment with one or more gold(I) complexes or a pharmaceutical composition thereof, the size of a tumor, whether by volume, weight or diameter, is reduced by at least 5%, 10%, 15%, 20%, 25%, 30%, 40%, 50%, 60%, 70%, 75%, 80%, 85%, 90%, 95%, 99% or 100%, relative to the tumor size before treatment. In other embodiments, after treatment with the one or more gold(I) complexes of a pharmaceutical composition thereof, the size of a tumor does not reduce but is maintained the same as the tumor size before treatment. Methods of assessing tumor size include but are not limited to CT Scan, MRI, DCE-MRI and PET Scan.

In some embodiments, the method for treating cancer and other proliferative disorders involves the administration of a unit dosage or a therapeutically effective amount of one or more of gold(I) complexes or a pharmaceutical composition thereof to a mammalian subject (preferably a human subject) in need thereof. As used herein, "a subject in need thereof" refers to a mammalian subject, preferably a human subject, who has been diagnosed with, is suspected of having, is susceptible to, is genetically predisposed to or is at risk of having at least one form of cancer. Routes or modes of administration are as set forth herein. The dosage and treatment duration are dependent on factors such as bioavailability of a drug, administration mode, toxicity of a drug, gender, age, lifestyle, body weight, the use of other drugs and dietary supplements, cancer stage, tolerance and resistance of the body to the administered drug, etc., then determined and adjusted accordingly. The one or more of gold(I) complexes or a pharmaceutical composition thereof may be administered in a single dose or multiple individual divided doses. In some embodiments, the interval of time between the administration of gold(I) complexes or a pharmaceutical composition thereof and the administration of one or more additional therapies may be about 1-5 minutes, 1-30 minutes, 30 minutes to 60 minutes, 1 hour, 1-2 hours, 2-6 hours, 2-12 hours, 12-24 hours, 1-2 days, 2 days, 3 days, 4 days, 5 days, 6 days, 7 days, 1 week, 2 weeks, 3 weeks, 4 weeks, 5 weeks, 6 weeks, 7 weeks, 8 weeks, 9 weeks, 10 weeks, 15 weeks, 20 weeks, 26 weeks, 52 weeks, 11-15 weeks. 15-20 weeks, 20-30 weeks, 30-40 weeks, 40-50 weeks, 1 month, 2 months, 3 months, 4 months 5 months, 6 months, 7 months, 8 months, 9 months, 10 months, 11 months, 12 months, 1 year, 2 years, or any period of time in between. In certain embodiments, dinuclear gold(I) compounds and one or more additional therapies are administered less than 1 day, 1 week, 2 weeks, 3 weeks, 4 weeks, one month, 2 months, 3 months, 6 month, 1 year, 2 years, or 5 years apart.

In certain embodiments, a gold(I) complex of the present disclosure or a pharmaceutical composition thereof may be used in combination with one or more other antineoplastic or chemotherapeutic agents. A non-limiting list of examples of chemotherapeutic agents are aflibercept, asparaginase, bleomycin, busulfan, carmustine, chlorambucil, cladribine, cyclophosphamide, cytarabine, dacarbazine, daunorubicin, doxorubicin, etoposide, fludarabine, gemcitabine, hydroxyurea, idarubicin, ifosamide, irinotecan, lomustine, mechclorethamine, melphalan, mercaptopurine, methotrexate, mitomycin, mitoxantrone, pentostatin, procarbazine, 6-thioguanine, topotecan, vinblastine, vincristine, retinoic acid, oxaliplatin, cis-platin, carboplatin, 5-FU (5-fluorouracil), teniposide, amasacrine, docetaxel, paclitaxel, vinorelbine, bortezomib, clofarabine, capecitabine, actinomycin D, epirubicine, vindesine, methotrexate, tioguanine (6-thioguaniue), tipifarnib. Examples for antineoplastic agents which are protein kinase inhibitors include imatinib, erlotinib, sorafenib, sunitinib, dasatinib, nilotinib, lapatinib, gefitinib, temsirolimus, everolimus, rapamycine, bosutinib, pzopanib, axitinib, neratinib, vatalanib, pazopanib, midostaurin and enzastaurin. Examples for antineoplastic agents which are antibodies comprise trastuzumab, cetuximab, panitumumab, rituximab, bevacizumab, mapatumumab, conatumumab, lexatumumab and the like.

EXAMPLES

The following examples are provided is illustrations of the disclosure and to provide those of ordinary skill in the art with specific preferred methods of synthesizing and characterizing gold(I) complexes within the scope of the present disclosure, and are not intended to limit the scope of what the applicants regard as their disclosure and the scope of the appended claims.

Example 1

Materials and Methods

Chemicals and solvents used in the synthesis were of analytical grade and were used without further purification. All the reactions were carried under normal ambient conditions. All chemicals were obtained from Sigma-Aldrich St. Louis, Mo. United States and Strem Chemicals, Massachusetts, United States.

Elemental analyses were performed on Perk in Elmer Series 11 (CHNS/O), Analyzer 2400. The solid state FTIR spectra of free ligands and their corresponding gold(I) complexes were recorded on a Perkin-Elmer FTIR 180 spectrophotometer or NICOLET 6700 FTIR using KBr pellets over the range 4000-400 $cm^{-1}$.

$^1$H, $^{13}$C and $^{31}$P NMR spectra were recorded on a LAMBDA 500 spectrophotometer operating at 500.01, 125.65 and 200.0 MHz respectively; corresponding to a magnetic field of 11.74 T. Tetramethylsilane (TMS) was used as an internal standard for $^1$H and $^{13}$C NMR measurements. Triphenylphosphine (TPP) was used as an external standard for $^{31}$P NMR measurement.

The $^{13}$C NMR spectra were obtained with $^1$H broadband decoupling. The spectral conditions were: 32 k data points, 0.967 s acquisition time, 1.00 s pulse delay and 45° pulse angle. The structure of the gold(I) precursor compound is shown in FIG. 1A while structures of the free ligands used in this disclosure are as shown in FIGS. 1B-1E. The $^1$H, $^{13}$C and $^{31}$P NMR chemical shifts of metal precursors and free ligands are given in Tables 1 and 2. The chemical structures of the synthesized complexes (A1-A4) are given in FIGS. 2A-2D.

TABLE 1

Solution $^1$H NMR chemical shifts (ppm) of the free gold(I) metal precursors and free ligand molecules.

| Compound | H—(CH$_3$) | H—(CH$_2$) | H—(Ph) |
|---|---|---|---|
| [t-Bu$_3$PAuCl] | 1.52 | — | — |
| NaS$_2$CN(CH$_3$)$_2$•H$_2$O | 3.55 | — | — |
| NaS$_2$CN(C$_2$H$_5$)$_2$•3H$_2$O | 1.23 | 4.03 | — |
| NaS$_2$CN(C$_7$H$_7$)$_2$•xH$_2$O | — | 4.98 | 7.01-7.22 |
| [(DPPM)(AuCl)$_2$] | — | 2.49 | 7.39-7.76 |

TABLE 2

Solution $^1$C and $^{31}$P NMR chemical shifts (ppm) of the free gold(1) metal precursors and free ligand molecules.

| Compound | C—(CH$_3$) | C—(CH$_2$) | C—(Ph) | C(C—P) | C(C=S) | $^{31}$P |
|---|---|---|---|---|---|---|
| [t-Bu$_3$PAuCl] | 32.23 | — | — | 39.42 | — | −6.00 |
| NaS$_2$CN(CH$_3$)$_2$•H$_2$O | 45.12 | — | — | — | 212.82 | — |
| NaS$_2$CN(C$_3$H$_5$)$_2$•3H$_2$O | 12.31 | 49.61 | — | — | 206.7 | — |
| NaS$_2$CN(C$_7$H$_7$)$_2$•H$_2$O | 56.9 | — | 127-137 | — | 213.53 | — |
| [(DPPM)(AuCl)$_2$] | — | 24.60 | 128-133 | — | — | 40.20 |

Example 2

Synthesis of Complex (A1), [t-Bu$_3$PAuS$_2$CN(C$_7$H$_7$)$_2$]

[t-Bu$_3$PAuCl] (0.217 g, 0.05 mmol) in 10 mL of dichloromethane was added in sodium dibenzyldithiocarbamate (0.136 g, 0.05 mmol) in 15 mL of ethanol at room temperature. Upon continuous stirring the reaction mixture for 3 h, the transparent light yellow solution was obtained, filtered to avoid any impurity and kept undisturbed for crystallization by slow evaporation at room temperature. The colorless block like crystals was obtained after seven days. A suitable quality crystal was chosen for X-ray diffraction analysis. Yield: 0.312 g, (93%). Anal. Calc. for C$_{27}$H$_{41}$AuNPS$_2$: C, 48.28; H, 6.15; N, 2.09; S, 9.54; Found: C, 48.17; H, 6.33; N, 2.02; S, 9.43. IR $cm^{-1}$; 3035 (w), 2995 (m), 2905 (m), 1491 (s), 1456 (s), 1378 (m), 1213 (s), 1170 (m), 1022 (m), 972 (s), 806 (m), 521 (s), 478 (m). NMR (CDCl$_3$-d$_1$): $^1$H, δ 1.57 (27H, C(2)H), 5.17 (4H, C(4)H), 7.32-7.34 (20H, H(Ph)); $^{13}$C, δ 32.29 C(2), 39.40 C(1), 55.79 C(4), 127.35-136.30 C(Ph), and 210.15 C(3); $^{31}$P: δ −7.83.

Example 3

Synthesis of Complex (A2), [(DPPM)Au$_2$(S$_2$CN(CH$_3$)$_2$)$_2$]

[μ-Bis(diphenylphosphino)methane]dichlorodigold(I), [(DPPM)(AuCl)$_2$] (0.425 g, 0.05 mmol) in 10 mL CH$_2$Cl$_2$ was added in Sodium dimethyldithiocarbamate monohydrate (0.144 g, 0.10 mmol) in 15 mL $C_2H_5OH$ at room temperature. Upon continuous stirring the reaction mixture for 3 h, the transparent yellow solution was obtained, filtered to avoid any impurity and kept undisturbed for crystallization by slow evaporation at room temperature. The yellow very small crystals were obtained after five days. Anal. Calc. for $C_{31}H_{34}Au_2N_2P_2S_4$: C, 36.55; H, 3.36; N, 2.75; S, 12.59; Found: C, 36.45; H, 3.53; N, 2.87; S, 12.68. Yield: 0.397 g, (78%). IR $cm^{-1}$: 3038 (w), 2980 (w), 2917 (w), 1481 (m), 1432 (s), 1370 (m), 1270 (m), 1147 (w), 1099 (m), 970 (m), 918 (w), 550 (s), 479 (m). NMR (DMSO-$d_6$): $^1H$, δ 2.49 (2H, C(1)H), 4.47 (12H, C(3)H), 7.31-7.79 (20H, H(Ph)); $^{13}C$, δ 30.68 C(1), 44.76 C(3), 128.78-133.25 C(Ph), and 208.15 C(2); $^{31}P$: δ 39.66.

Example 4

Synthesis of Complex (A3), [(DPPM)$Au_2$($S_2$CN($C_2H_5$)$_2$)$_2$]

[μ-Bis(diphenylphosphino)methane]dichlorodigold(I), [(DPPM)(AuCl)$_2$] (0.425 g, 0.05 mmol) in 10 mL $CH_2Cl_2$ was added in Sodium diethyldithiocarbamatetrihydrate (0.226 g, 0.10 mmol) in 15 mL of $C_2H_5OH$ at room temperature. Upon continuous stirring the reaction mixture for 3 h, the transparent yellow solution was obtained on the addition of 3 mL water was for clarity, filtered to avoid any impurity and kept undisturbed for slow evaporation at room temperature. After three days yellow semi-crystalline product was obtained. Anal. Calc. for $C_{35}H_{42}Au_2N_2P_2S_4$; C, 39.11; H, 3.94; N, 2.61; S, 11.93; Found: C, 39.05; H, 3.83; N, 2.57; S, 11.68. Yield: 0.392 g, (73%). IR $cm^{-1}$: 3043 (w), 2970 (w), 2921 (w), 1486 (m), 1432 (s), 1374 (m), 1265 (m), 1137 (w), 1087 (m), 982 (m), 908 (m), 560 (s), 478 (m), NMR (DMSO-$d_6$): $^1H$, δ 1.22 (12H, C(4)H), 2.49 (2H, C(1)H, 4.49 (8H, C(3)H, 7.33-7.79 (20H, H(Ph)); $^{13}C$, δ 12.17 C(4), 30.66 C(1), 49.06 C(3), 128.83-133.29 C(Ph), and 206.62 C(2); $^{31}P$: δ 40.69.

Example 5

Synthesis of Complex (A4), [(DPPM)$Au_2$($S_2$CN($C_7H_7$)$_2$)$_2$]

[μ-Bis(diphenylphosphino)methane]dichlorodigold(I), [(DPPM)(AuCl)$_2$] (0.425 g, 0.05 mmol) in 10 mL $CH_2Cl_2$ was added in sodium diebenzyldithiocarbamatetrihydrate (0.272 g, 0.10 mmol) in 15 mL of $C_2H_5OH$ at room temperature. Upon continuous stirring the reaction mixture for 3 h, a turbid solution was obtained initially. The transparent pale yellow solution was obtained on addition of 3 mL of water for the removal of turbidity, filtered to avoid any impurity and kept in dark for slow evaporation. The bright yellow crystalline product was obtained after seven days. Anal. Calc. for $C_{55}H_{50}Au_2N_2P_2S_4$: C, 49.93; H, 3.81; N, 2.12; S, 9.69; Found: C, 49.85; H, 3.85; N, 2.15; S, 9.58. Yield: 0.549 g, (83%). IR $cm^{-1}$: 3025 (w), 2919 (w), 1489 (s), 1432 (s), 1351 (m), 1209 (s), 1147 (m), 1025 (m), 970 (s), 810 (w), 518 (m), 479 (m). NMR (DMSO-$d_6$): $^1H$, δ 2.49 (2H, C(1)H), 5.00 (8H, C(3)H), 7.23-7.83 (40H, H(Ph)); $^{13}C$, δ 30.99 C(1), 56.10 C(3), 126.88-135.96 C(Ph), and 208.54 C(2); $^{31}P$: δ 40.20.

Example 6

Stability of Synthesized Gold(I) Complexes

Complexes (A1) and (A2) were dissolved in DMSO-$d_6$ and analyzed by $^1H$ and $^{13}C$ {1H} NMR measurements. The extent of decomposition over time was determined by comparing the NMR spectra collected after 1, 6, 12, 24, 48 and 72 h. No significant change in the chemical shifts and the splitting patterns of compounds (A1) and (A2) was observed in their time dependent $^1H$ NMR spectra.

Additionally, Complexes (A1)-(A4) were found to be completely soluble in polar organic solvents i.e. DMSO and DMF; and sparingly soluble in water.

Example 7

X-Ray Diffraction Studies of Synthesized Gold(I) Complexes

Figure 3:
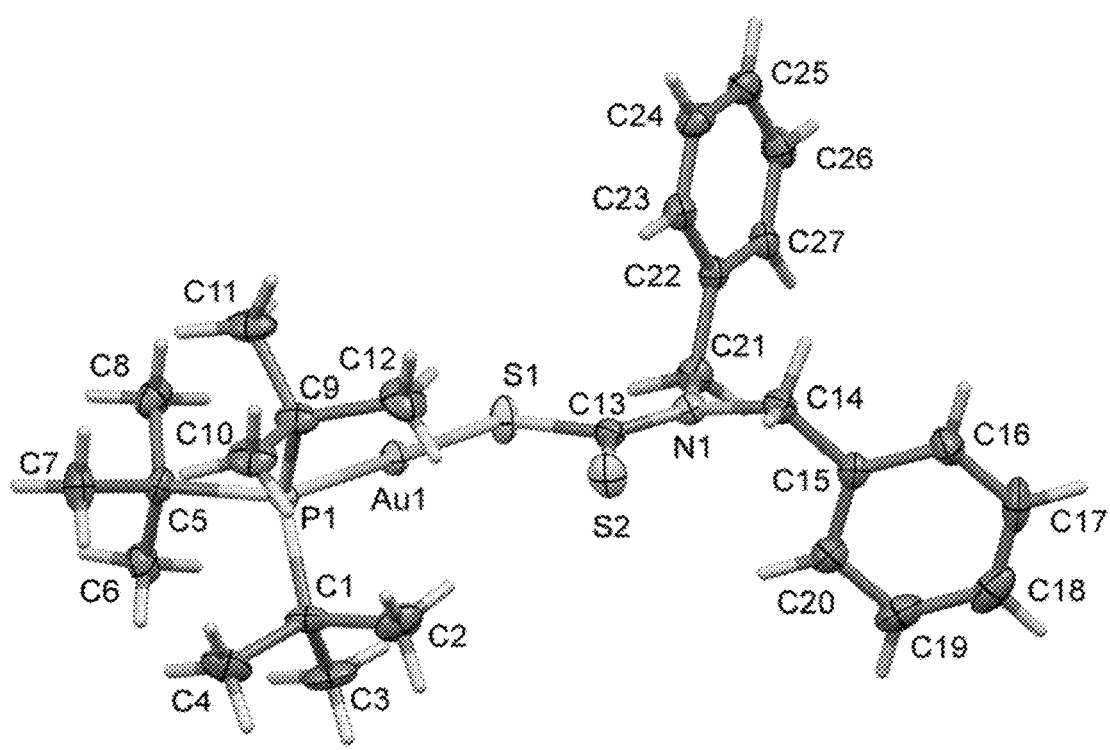
FIG. 3 is a graphic image showing the molecular structure of complex (A1) with atom labeling and displacement ellipsoids drawn at a 50% probability level.

Pale yellow plate-like crystals of Complex (A1) were obtained by recrystallization of the final product using a mixture of solvents i.e. $C_2H_5OH$ and $H_2O$ in 4:1 v/v ratio under slow evaporation at room temperature. The intensity data were collected at 173K (−100° C.) on a Stoe Mark II-Image Plate Diffraction System equipped with a two-circle goniometer using MoKα graphite mono chromated radiation (λ=0.71073 Å) [Stoe & Cie, X-Area & X-RED32, GmbH, Darmstadt, Germany, (2009)—incorporated herein by reference in its entirety]. The structure was solved by direct methods with SHELXS-97. The refinement and all further calculations were carried out with SHELXL-2013 [G. M. Sheldrick, Acta Cryst., A64 (2008) 112—incorporated herein by reference in its entirety]. The C-bound H-atoms were included in the calculated positions and treated as riding atoms: C—H=0.95, 0.99 and 0.98 Å for CH (aromatic), $CH_2$ and $CH_3$, respectively, with $U_{iso}(H)$=1.5 $U_{eq}$(C-methyl) and =1.2 $U_{eq}$(C) for other H-atoms. The non-H atoms were refined anisotropically, using weighted full-matrix least-squares on $F^2$. A semi-empirical absorption correction was applied using the MULscanABS routine in PLATON [A. L. Spek, Acta Cryst., D65 (2009) 148—incorporated herein by reference in its entirety]. FIG. 3, which is generated using the program MERCURY, is a graphic image showing the molecular structure of complex (A1) with atom labeling and displacement ellipsoids drawn at a 50% probability level [C. F. Macrae, I. J. Bruno, J. A. Chisholm, P. R. Edgington, P. McCabe, E. Pidcock, L. Rodriguez-Monge, R. Taylor, J. van de Streek and P. A. Wood, J. Appl. Cryst., 41 (2008) 466—incorporated herein by reference in its entirety]. A summary of crystal data and refinement details for gold(I) complex (A1) are given in Table 3. Selected bond lengths and bond angles are given in Table 4.

In the X-ray structure of Complex (A1) shown in FIG. 3, gold(I) is shown to be coordinated with one P donor atom of tri-tert-butylphosphine and S donor atom of dibenzyldithiocarbamate ligand molecules. The Au—S and Au—P bond distances are 2.3365 (13) and 2.2824 (13) Å respectively. The Au—P and Au—S bond distances are comparable with [$Et_3$PAu($S_2$C$NEt_2$)] complex [S. Y. Ho and E. R. T. Tiekink, Z. Kristallogr, 220 (2005) 342—incorporated herein by reference in its entirety]. The geometry around Au(I) metal atom is linear and similar to other analogous Au(I) complexes [I. Sänger, H.-W. Lerner, T. Sinke and M. Bolte, Acta Cryst., E68 (2012) m708; P. Lu, T. C. Boorman, A. M. Z. Slawin and I. Larrosa, J. Am. Chem. Soc., 132 (2010) 5580; R. E. Marsh, Acta Cryst., B58 (2002) 893; H. Schmidbaur, B. Brachthiuser, O. Steigelmann, and H. Beruda, Chem. Ber., 125(1992) 2705—each incorporated herein by reference in its entirety]. S—Au—P bond angle is 178.33 (5)° in the molecular structure of [t-$Bu_3$PAu$S_2$CN($C_7H_7$)$_2$] or Complex (A1) which is very close to angle of 180° for ideal linear geometry. Hence, the complex (A1) shows a small deviation from ideal linear geometry around gold(I) atom (Table 4) and confirms the presence of distorted linear geometry in this molecule.

TABLE 2

Crystallographic characteristics, experimental and structure refinement details for crystal structure of Complex (A1).

| Parameters | Complex 1 |
| --- | --- |
| Empirical formula | $C_{27}H_{41}AuNPS_2$ |
| Empirical formula weight | 671.66 |
| Crystal size/mm | 0.45 × 0.30 × 0.07 |
| Wavelength/Å | 0.71073 |
| Temperature/K | 173 |
| Crystal symmetry | Orthorhomhic |
| Space group | Pbca |
| a/Å | 12.3157 (12) |
| b/Å | 19.6569 (19) |
| c/Å | 22.945 (2) |
| V/Å$^3$ | 6375.6 (4) |
| Z | 8 |
| $D_c$/Mg m$^{-3}$ | 1.606 |
| μ(Mo—Kα)/mm$^{-1}$ | 5.52 |
| F(000) | 2688 |
| θ Limits/° | 1.8-26.2 |
| Collected reflections | 17654 |
| Unique reflections | 3454 |
| Observed reflections | 5296 |
| Goodness of fit on F$^2$ | 0.79 |
| $R_1[F^2 > 2\sigma(F^2)]$ | 0.028 |
| $wR_2(F^2)$ | 0.062 |
| Largest diff. peak, hole/e Å$^{-3}$ | 1.08-0.79 |

TABLE 3

Selected bond distance (Å) and bond angles (°) for Complex (A1).

| Bond Length (Å) | | Bond Angles (°) | |
| --- | --- | --- | --- |
| Au1—P1 | 2.2824 (13) | P1—Au1—S1 | 178.33 (5) |
| Au1—S1 | 2.3365 (13) | C13—S1—Au1 | 100.26 (16) |
| S1—C13 | 1.749 (5) | C5—P1—C1 | 110.4 (2) |
| S2—C13 | 1.701 (5) | C5—P1—C9 | 110.4 (2) |
| | | C1—P1—C9 | 109.7 (2) |
| | | C5—P1—Au1 | 110.40 (16) |
| | | C1—P1—Au1 | 106.82 (18) |
| | | C9—P1—Au1 | 109.03 (19) |

Example 8

Chemistry and Spectroscopic Characterization of Synthesized Gold(I) Complexes

Addition of dibenzyl dithiocarbamate to tri-tert butylphosphine gold(I) chloride afforded the formation of mononuclear gold(I) crystalline complex (A1). Moreover, addition of dimethyl dithiocarbamate, diethyl dithiocarbamate, dibenzyl dithiocarbamate to [μ-Bis(diphenylphosphino) methane]dichlorodigold(I) afforded the formation of three binuclear gold(I) complexes (A1)-(A3) respectively in good yields. Binuclear bisphosphine gold(I) complexes (A2) and (A3) contain small alkyl groups i.e. methyl and ethyl in dialkyl dithiocarbamate in order to examine the steric effects on anticancer activities. On the other hand, mononuclear monophosphine gold (I) complex (A1) and binuclear bisphosphine gold(I) complex (A4) contain bulky aryl group i.e. benzyl in diaryl dithiocarbamate to evaluate the steric effects on in vitro cytotoxicity.

Dithiocarbamate compounds can be identified via the presence of certain absorbance peaks primarily v(C—N) and v(C—S). The region 1480-1550 cm$^{-1}$ is primarily associated with the $R_2N$—CSS 'thioureide' band in the infrared spectra of dithiocarbamate compounds which defines the carbon-nitrogen bond order between a single bond at 1250-1350 cm$^{-1}$ and a double bond at 1640-1690 cm$^{-1}$ [A. J. Odola and J. A. O. Woods, J. Chem., Pharm. Res., 3 (2011)—incorporated herein by reference in its entirety].

The distinctive thioureide band, v(C—N) was detected at 1456 cm$^{-1}$, 1481 cm$^{-1}$, 1486 cm$^{-1}$ and 1489 cm$^{-1}$ in complexes (A1)-(A4) respectively. Since these frequency modes lie in between those associated with single C—N and double C=N bonds, hence the partial double bond character of 'thioureide' bond was confirmed for all gold(I) complexes [F. Jian, Z. Wang, Z. Bai, X. You, H. Fun, K. Chinnakali and L. A. Razak, Polyhedron, 18 (1999) 3401—incorporated by reference in its entirety]. The presence of the 'thioureide' band between 1545-1430 cm$^{-1}$ suggest a considerable double bond character in the C . . . N bond vibration of the $S_2C$—$NR_2$ group [A. Jayaraju, M. M. Ahamad, R. M. Rao, J. Sreeramulu, Der Pharma Chemica, 4 (2012) 1191—incorporated herein by reference in its entirety]. This strong absorption band (1542-1480 cm$^{-1}$) is known as the thioureide ion band. The band appears intermediate within C—N single bond (C—N: 1063-1261 cm$^{-1}$) and double bond (C=N: 1640-1690 cm$^{-1}$) wave numbers. Such characteristic band shows the partial double bond feature which characterizes the formation of dithiocarbamato ($S_2C$—$NR_2$)$^-$ anion. The stretching vibration corresponds to this partial double bond due to the partial delocalization of electron density within the dithiocarbamate [H. Nabipour, S. Ghammamy, S. Ashuri and Z. S. Aghbolagh, J. Org. Chem., 2 (2010) 75—incorporated herein by reference in its entirety]. A strong absorption in this region of the FTIR spectrum results into a strong signal of dithiocarbamato gold(I) complexes [J. Chatt, L. A. Duncanson and L. M. Venanzi, Nature, 177 (1956) 1042—incorporated herein by reference in its entirety].

The C=S thiocarbonyl stretching splits into two peaks (doublet) with medium intensity at 1022 cm$^{-1}$ and 972 cm$^{-1}$; and 995 cm$^{-1}$; 1087 cm$^{-1}$; and 982 cm$^{-1}$; and 1025 cm$^{-1}$ and 970 cm$^{-1}$ for complexes (A1)-A(4) respectively. The splitting of stretching band is found within the range of 1099-970 cm$^{-1}$ due to the prevailing contribution of (C . . . S). Such splitting in the v(C—S) bands clearly indicates the monodentate nature of dialkyldithiocarbamate ligands in the synthesized complexes [I. Raya, I. Baba, B. M. Yamin, Malaysia J. Analytical Sciences (MJAS), 10 (2006) 93; W. Haas, and T. Schwarz, Microchem. Ichonal. Acta, 58 (1963) 253; D. C. Onwudiwe and P. A. Ajibade, Polyhedron, 29 (2010) 1431—each incorporated herein by reference in its entirety]. The spectroscopic data suggests monodentate modes of coordination for the dithiocarbamate ligands in complexes (A1)-(A4) in analogy of compound [$Ph_2P(CH_2)_2PPh_2$] ($AuS_2CNEt_2$)$_2$ [J. W. Faamaua and E. R. T. Tiekinka, J. Coord. Chem., 31(2) (1994) 93—incorporated herein by reference in its entirety].

In addition to the polar thioureide ion $S_2C$=$N^+R_2$ band, the common bands for sp$^3$ and sp$^2$ hybridized C—H stretches are observed within 2995-22917 cm$^{-1}$ and above 3000 cm$^{-1}$ respectively which are very comparable to those of sodium salt of diethyldithiocarbamate [C. J. Pouchert, Aldrich Library of FT-IR Spectra, 2nd ed., Aldrich Chemical Company, Milwaukee, 1 (1997)—incorporated herein by reference in its entirety].

In complexes (A1) and (A4), the stretch bands of aromatic (phenyl) and the saturated aliphatic C—H methyl group of coordinated dialkyl/diaryldithiocarbamate correspond above and below 3000 cm$^{-1}$. The C—H methyl groups have characteristic bending absorptions at 1370 cm$^{-1}$ and 1374 cm$^{-1}$ in complexes (A2) and (A3) respectively. The C—H bending band(s) associated C—H stretching band(s) are often determining factor whether methyl groups are present in a molecule or not. The coordinated C—H(—CH$_2$—) methylene stretching bands of diethyl dithiocarbamate and dibenzyl dithiocarbamate occur at 2983 cm$^{-1}$, 2921 cm$^{-1}$ and 2919 cm$^{-1}$ respectively; and their corresponding bending bands appears at 1378 cm$^{-1}$, 1432 cm$^{-1}$ and 1332 cm$^{-1}$ for complexes (A1), (A3) and (A4) respectively [D. L. Pavia, G. M. Lampman, S. G. Kriz, Introduction to Spectrochemistry, 3rd Ed., Thomson Learning, USA, (2001) 30; R. M. Silverstein, F. X. Webster, Spectrometric Identification of Organic Compounds, 6th ed., (Wiley, New York, 1998); T. W. G. Solomons, C. Fryhle Organic Chemistry, 7th ed., Wiley, New York, 2001; K. N. Kouroulis, S. K. Hadjikakou, N. Kourkoumelis, M. Kubicki, L. Male, M. Hursthouse, S. Skoulika, A. K. Metsios, V. Y. Tyurin, A. V. Dolganov, E. R. Milaevag and N. Hadjiliadis, Dalton Trans., (2009) 10446; E. A. Allen and W. Wilkinson, Spectrochim. Acta, 2 (1972) 2257; I. S. Butler, A. Neppel, K. R. Plowman and C. F. Shaw, J. Raman Speetrosc., 15 (1984) 310; A. G. Jones and D. B. Powell, Spectrochim. Acta, 30 (1984) 563—each incorporated herein by reference in its entirety].

The $^1$H NMR chemical shifts of metal precursors [t-Bu$_3$PAuCl], [(DPPM)(AuCl)$_2$] and free dialkyl/diaryldithiocarbamate ligands are given in Table 1. Small upfield and downfield shifts for the mono and bisphosphine coordinated ligands protons have been observed for complexes (A1)-(A4); with respect to the chemical shifts of free metal precursor as given in synthesis part of experimental section for these complexes. In all four complexes slight downfield and upfield shifts for proton(s) of the coordinated dimethyl dithiocarbamate, diethyl dithiocarbamate and dibenzyldithiocarbamate have also been seen in gold(I) complexes (A1)-(A4) respectively in comparison to free dialkyl/diaryldithiocarbamate ligands (Table 1).

The $^{13}$C and $^{-}$P NMR chemical shifts of metal precursors [t-Bu$_3$PAuCl], [(DPPM)(AuCl)$_2$] and free dialkyl/diaryldithiocarbamate ligands are given in Table 2. The $^{13}$C NMR spectra of complexes (A1)-(A4) showed many resonances as given in synthesis part of experimental section for these complexes. There are up-field chemical shifts of CH$_3$, CH$_2$ and C=S carbons of coordinated dialkyldithiocarbamate with respect to free dialkyl/diaryldithiocarbamate ligands. The $^{13}$C chemical shifts of C=S carbon of dimethyl thiocarbamate, diethyl thiocarbamate and dibenzyl thiocarbamate are observed in the range 206-210 ppm. The upfield shifts of C=S carbon are additional confirmations for the coordination of dialkyl/diaryl dithiocarbamates ligands in the synthesized complexes (A1)-(A4).

Example 9

Cell Cultures

A549, HeLa and HCT15 human cancer cells were seeded and maintained in triplicate at 4×10$^3$ cells/well in 100 µL DMEM (Dulbecco's Modified Eagle's Medium) containing 10% FBS (Fetal Bovine Serum) in 96-wells tissue culture plate and incubated for 72 h at 37° C. 5% CO$_2$ in air and 90% relative humidity in CO$_2$ incubator.

Example 10

MTT Assays for Anticancer Activity of Cisplatin, Gold(I) Precursor Complex A0 and Synthesized Gold(I) Complexes A1-A4

100 µL of cisplatin, gold(I) precursor Complex A0 and gold(I) Complexes (A1)-(A4) in 50, 25, 12.5 and 6.25 µg/mL concentrations, prepared in DMEM, were added to 5000 cancer cells after incubation. The resultant cultures were incubated for 24 h. The medium of wells was discarded. 100 µL DMEM containing MTT (3-(4,5-Dimethylthiazol-2-Yl)-2,5-Diphenyltetrazolium Bromide) (5 mg/mL) was added to the wells and incubated in CO$_2$ incubator at 37° C. in dark for 4 h. After incubation, a purple colored formazan (artificial chromogenic dye, product of the reduction of water insoluble tetrazolium salts e.g., MMT by dehydrogenases and reductases) in the cells is produced and appeared as dark crystals in the bottom of the wells. The medium of culture was discarded from each well carefully to avoid disruption of monolayer. 100 µL of Dimethylsulphoxide (DMSO) was added in each well. The solution was thoroughly mixed in the wells to dissolve the formazan crystals which ultimately result into a purple solution. The absorbance of the 96-wells plate was taken at 570 nm with Lab systems Multiskan EX-Enzyme-linked immunosorbent assay (EX-ELISA) reader against a reagent blank. All data presented are mean±standard error of the mean (SEM).

Figure 4:
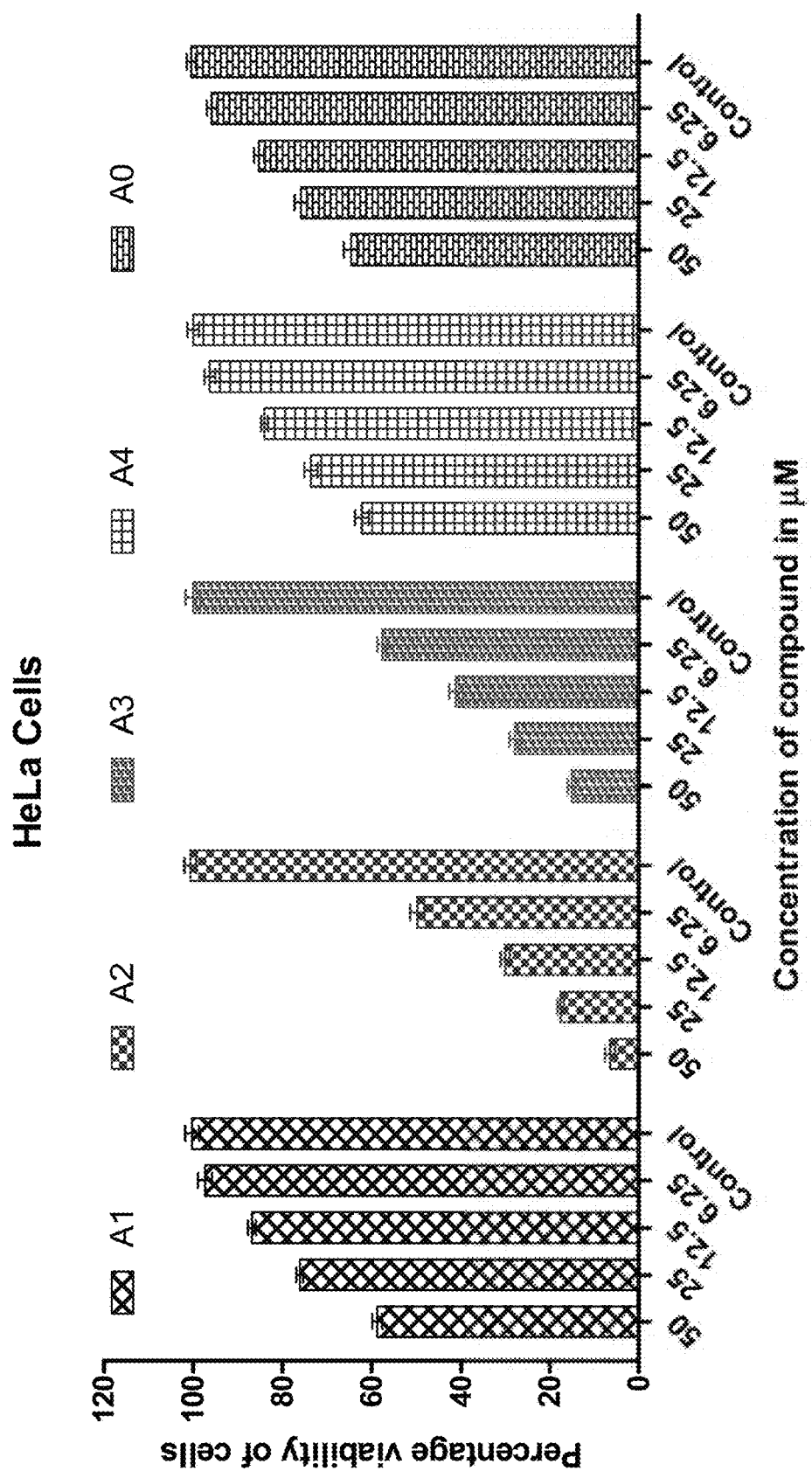
FIG. 4 is a bar graph showing the concentration dependent in vitro cytotoxic effect of complexes (A1)-(A4) on the viability of HeLa cancer cells.
Figure 5:
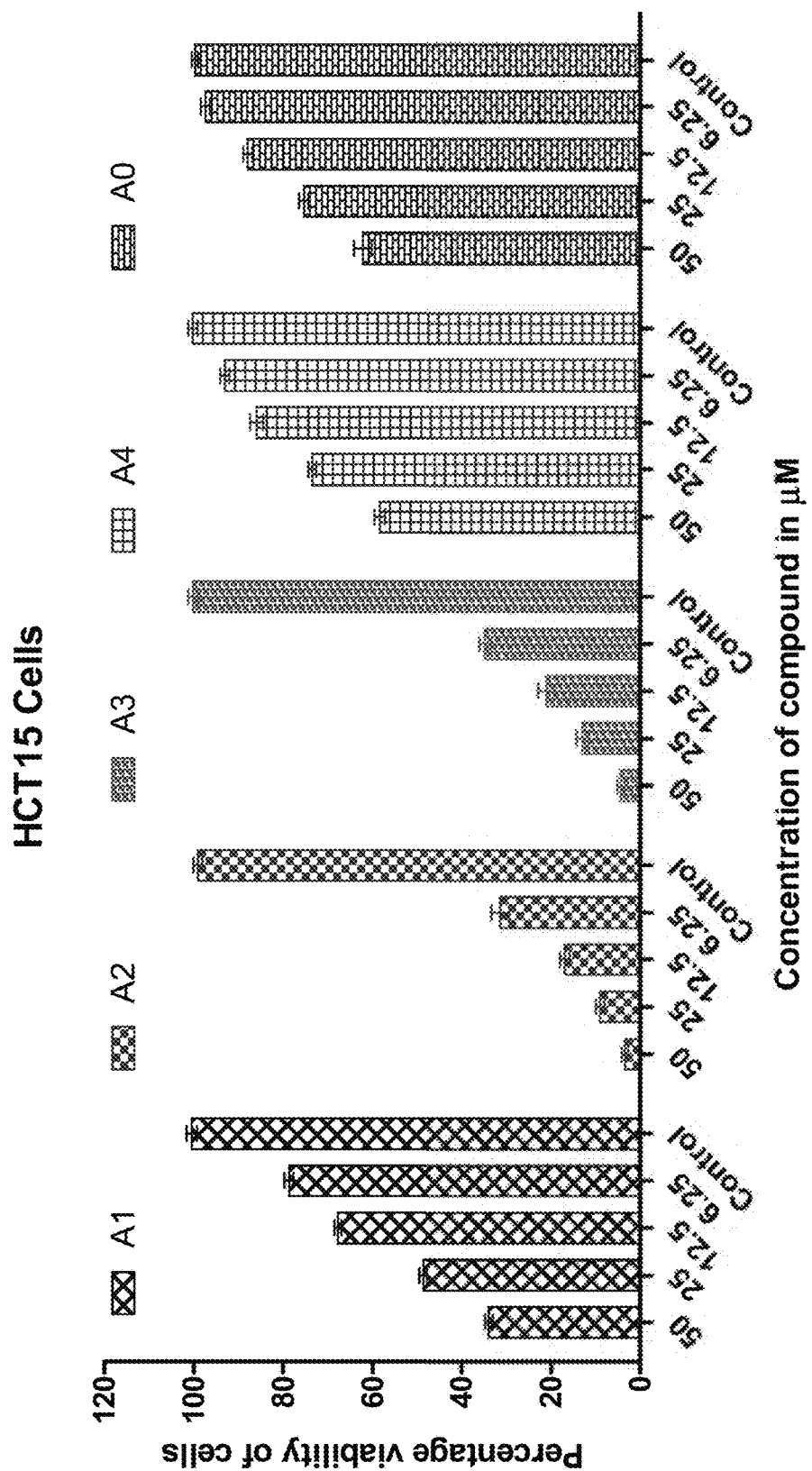
FIG. 5 is a bar graph showing the concentration dependent in vitro cytotoxic effect of complexes (A1)-(A4) on the viability of HCT15 cancer cells.
Figure 6:
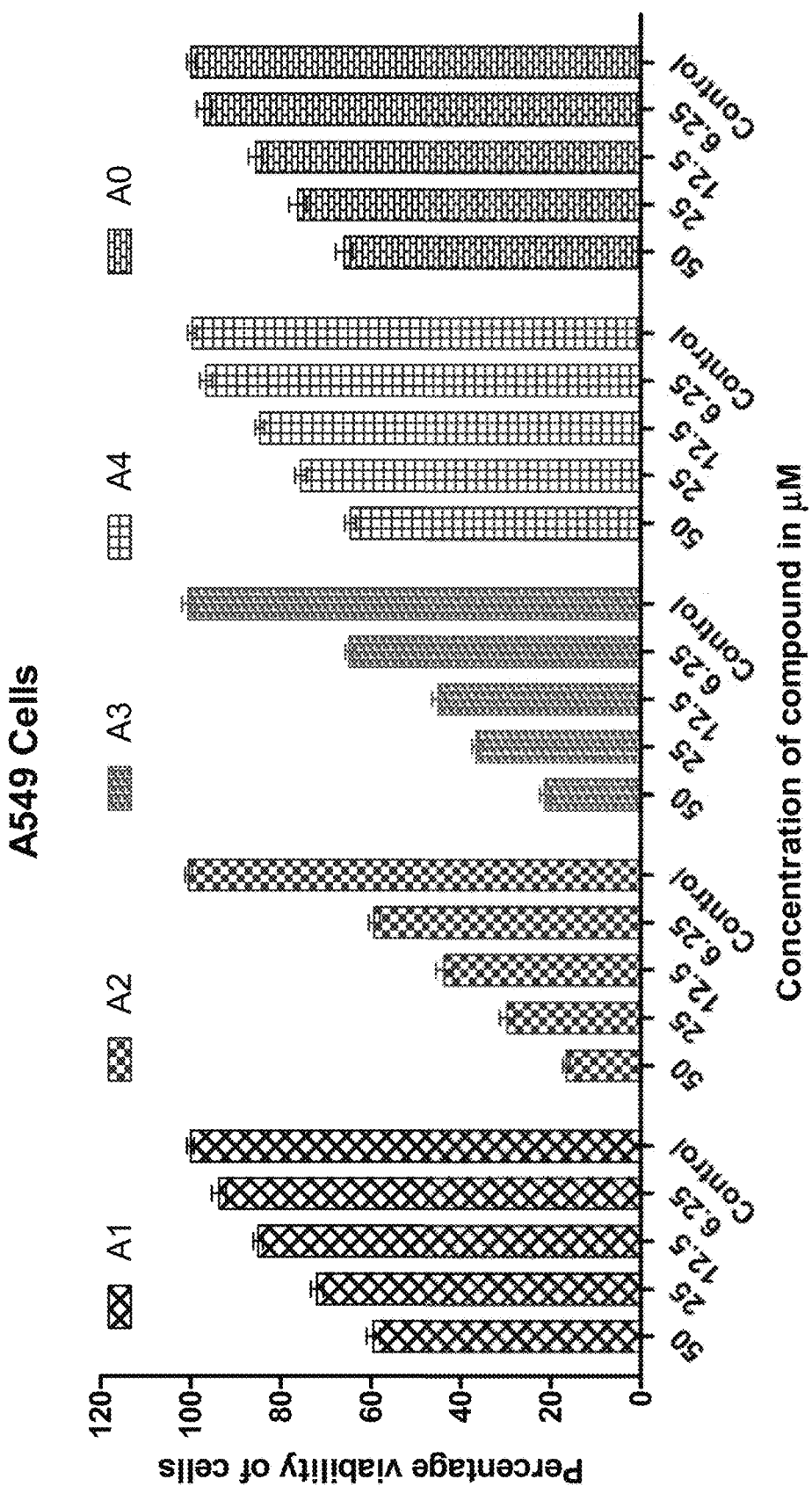
FIG. 6 is a bar graph showing the concentration dependent in vitro cytotoxic effect of complexes (A1)-(A4) on the viability of A549 cancer cells.

The concentration (dose) dependent in vitro cytotoxic effect was obtained by the specific increase in concentrations of cisplatin, gold(I) precursor (A0) and gold(I) Complexes (A1)-(A4) against a panel of human cancer cells. The viability of HeLa, HCT15 and A549 cancer cells versus concentrations of gold(I) complex is graphically presented in FIGS. 4, 5 and 6, respectively. Gold(I) precursor (A0) and synthesized complexes (A1)-(A4) invariably inhibited the proliferation of all cancer cells in a concentration dependent manner. Generally, the growth inhibition of cancer cells is higher for the synthesized complexes (A1)-(A4) in comparison to that of gold(I) precursor (A0). Particularly, the degree of anti-proliferation of gold(I) of the synthesized complexes (A2) and (A3) is significantly greater than those of the synthesized complexes (A1) and (A4) as illustrated in FIGS. 4-6.

The IC$_{50}$ values for cisplatin, gold(I) precursor (A0) and complexes (A1)-(A4) against three cancer lines are given in Table 4. The IC$_{50}$ data for the synthesized gold(I) complexes (A1)-(A4) against selected human cancer cell lines i.e. A549, HeLa and HCT15 are in the range of 1.3 to 132.7 µM. For comparative purposes, the IC$_{50}$ values of cisplatin for the same cell lines were also included.

TABLE 4

IC$_{50}$ data (µM) of cispaltin and gold(1) complexes (0-4) against A549, HeLa and HCT15 cancer cell lines.

| Complex | IC50 (µM) | | |
|---|---|---|---|
| | A549 | HeLa | HCT15 |
| Cisptatin | 41.6 | 19.4 | 29.5 |
| [(DPPM)(AuCl)$_2$](A0) | 136.6 | 108.5 | 148 |
| (A1) | 96.9 | 25.6 | 93.2 |
| (A2) | 5.4 | 1.3 | 9.5 |
| (A3) | 8.6 | 1.6 | 11.8 |
| (A4) | 105.8 | 93.2 | 132.7 |

The IC$_{50}$ values against A549 cell line were found to be 41.6, 136.6, 96.9, 5.4, 8.6 and 105.8 µM for cisplatin, gold (I) precursor (A0) and complexes (A1)-(A4) respectively. It is inferred from the $IC_{50}$ data that in vitro cytotoxicity of complexes (A2) and (A3) is significantly greater 15-25 times than gold (I) precursor (A0); and 5-8 times than cisplatin respectively. The $IC_{50}$ values of cisplatin, precursor (A0) and gold complexes (A1)-(A4) against HeLa cell line were found to be 19.4, 108.5, 25.6, 1.3, 1.6 and 93.2 µM respectively. A similar trend has been observed in HeLa cell line that in vitro cytotoxicity of complexes (A2) and (A3) in terms of $IC_{50}$ is improved almost 75 folds than gold (I) precursor; and 12-15 folds than cisplatin respectively. $IC_{50}$ values of cisplatin, gold precursor (A0), gold complexes (A1)-(A4) against HCT15 cell line were 29.5, 93.2, 9.5, 11.8, 132.7 and 148.0 µM respectively. Similarly, to A459 and HeLa cell lines, in vitro cytotoxicity of complexes (A2) and (A3) in terms of $IC_{50}$ is enhanced 12-16 times than gold (I) precursor; and 2-3 times than cisplatin. In short, the order of in vitro cytotoxicity is (A2)>(A3)>cisplatin>(A1)>(A4)>precursor (A0) against A549, HeLa and HCT15 cancer cell lines. It is pertinent to mention that the effectiveness trend of complexes (A2) and (A3) in terms of in vitro cytotoxicity against three cell lines is HeLa>A549>HCT15. It can be concluded from this studies that complexes (A2) and (A3) are the most effective cytotoxic agents against HeLa cancer cell line.

As far as the in vitro cytotoxicity against A549, HeLa and HCT15 cell lines is concerned, two out of four synthesized complexes (A2) and (A3) show much better anticancer activity than classical and well known anticancer drug cisplatin. The much better inhibition of growth of cancer cells by synthesized complexes than gold(I) precursor complex can be attributed to dithiocarbamate as labile co-ligands bonded with central gold(I) ions in synthesized complexes (A1)-(A4) by replacing chloride ions in these mononuclear and binuclear complexes.

As known in the art of drug design and discovery; selectivity and inhibition of target biomolecules is very important. In this regard the in vitro cytoxicity results in the present disclosure are fruitful and very encouraging for further exploration of anticancer activity of gold(I) complexes. In short, the $IC_{50}$ values of gold(I) complexes (A2) and (A3) having dialkyldithiocarbamate ligands show much better cytotoxicity than gold(I) complexes (A1) and (A4) having diaryldithiocarbamate ligands. The lower cytotoxic activity of gold(I) complexes (A1) and (A4) is due to bulky size and steric hindrance of diarylthiocarbamate ligands. The steric hindrance of bulky ligand makes the approach of gold(I) ions difficult to biomolecules in these complexes. Overall the anticancer activity of synthesized complexes against A549, HeLa and HCT15 human cancer cell lines are interesting and in µM range as found in previous anticancer studies of gold complexes [E. Barreiro, J. S. Casas, M. D. Couce, A. Sánchez, J. Sordo and E. M. Vázquez-López, J. Inorg. Biochem., 131 (2014) 68; R. Kivekäs, E. Colacio, J. Ruiz. J. D. López-González and P. León, Inorg. Chim. Acta., 159 (1989) 103; L. Ortego, F. Cardoso, S. Martins, M. F. Fillat, A. Laguna, M. Meireles, M. D. Villacampa and M. C. Gimeno, J. Inorg. Biochem., 130 (2014) 32; I. Ott, T. Koch, H. Shorafa, Z. Bai, D. Poeckel, D. Steinhilber and R. Gust, Org. Biomol. Chem., 3 (2005) 2282—each incorporated herein by reference in its entirety].

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The invention claimed is:

1. A method for inhibiting proliferation of prostate cancer cells, comprising:
    contacting the prostate cancer cells with a cytotoxic effective amount of a gold(I) complex represented by Formula (3), wherein Formula (3) is:

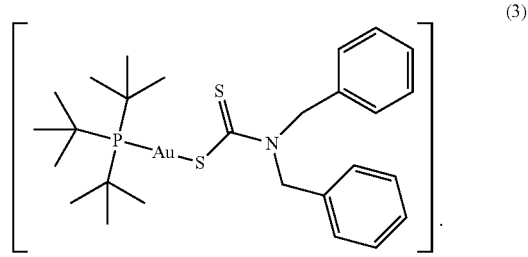

2. The method of claim 1, wherein the prostate cancer cells are human cells.

3. The method of claim 1, wherein the cytotoxic effective amount of the gold(I) complex is from 5 to 50 µM.

4. The method of claim 1, wherein the gold(I) complex exhibits an $IC_{50}$ of from 1 to 150 µM for inhibiting the proliferation and inducing the apoptosis of the prostate cancer cells.

5. The method of claim 1, wherein the prostate cancer cells are at least one selected from the group consisting of PC-3 cells and DU-145 cells.

* * * * *